United States Patent
Loozen et al.

(10) Patent No.: US 6,881,728 B1
(45) Date of Patent: Apr. 19, 2005

(54) 14-β, 17-α-HYDROXYMETHYLANDROSTANE DERIVATIVES AS ANDROGENS

(75) Inventors: Hubert Jan Jozef Loozen, AC Uden (NL); Dirk D. Leysen, Lommel (BE); Jaap van der Louw, En Oss (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/890,845

(22) PCT Filed: Mar. 2, 2000

(86) PCT No.: PCT/EP00/01755

§ 371 (c)(1),
(2), (4) Date: Sep. 25, 2001

(87) PCT Pub. No.: WO00/53619

PCT Pub. Date: Sep. 14, 2000

(30) Foreign Application Priority Data

Mar. 8, 1999 (EP) ............................................. 99200665

(51) Int. Cl.$^7$ .............................. A61K 31/56; C07J 1/00
(52) U.S. Cl. ....................... 514/177; 514/170; 514/171; 514/178; 514/182; 552/502; 552/650
(58) Field of Search ................................ 514/171, 177, 514/170, 178, 182; 552/611, 502, 650

(56) References Cited

U.S. PATENT DOCUMENTS 3,086,027 A    4/1963  Perelman et al.
4,002,746 A *  1/1977  Hughes et al. .............. 424/243
6,180,682 B1 * 1/2001 Place ........................ 514/841

FOREIGN PATENT DOCUMENTS

EP    0 277 676 A    8/1988
WO    WO 93 15104 A  8/1993

OTHER PUBLICATIONS

Okada, M. et al.: "Synthesis of 3. beta.–hydroxy–5.alpha.–card–20(22)–enoli de" Chemical and Pharmaceutical Bulletin, vol. 16, No. 11, 1968, pp. 2223–2227.
Shoppee, C. W.: "Abba des Diginigenins zu einem Kohlenwasserstoff Diginan CZ1H36", Helvetica Chimica Acta, vol. 27, 1944, pp. 246–260.
Chemical Abstracts, vol. 53, No. 12, Jun. 25, 1959, Columbus, Ohio, Abstract No. 11442a.
Da Silva Campos Neves, A.: "Study on The Partial Synthesis of Alderstone" & Bol. Escola Farm. Univ. of Coimbra, vol. 17, 1957, pp. 1–129. (Abstract Only).
Barton, D.H. et al.: "An Approach to the Partial Synthesis of Aldosterone From Steroids Lacking Substitutions at C18", Journal of the Chemical Society., No. 6, Jun. 1957, pp. 2698–2706.
Crabbe, P. et al, Can. J. Chem. 46, 349 (1968).
J. Chem. Soc., 361O (1962).

* cited by examiner

Primary Examiner—Barbara P. Badio
(74) Attorney, Agent, or Firm—William M. Blackstone

(57) ABSTRACT

Androgenic steroids having a (14β,17α-)-17-(hydroxymethyl) configuration, useful for the preparation of male contraceptives and pharmaceutical formulations for the treatment of androgen insufficiency.

5 Claims, No Drawings

14-β, 17-α-HYDROXYMETHYLANDROSTANE DERIVATIVES AS ANDROGENS

This application is a 371 of PCT/EP00/01755 filed Mar. 2, 2000.

The invention is in the field of steroid hormones. This is a relatively old field, in which a great many possible substitutions on a common steroid skeleton are known to lead to many different hormonal activities and medical utilities, and in which the basic structure-activity relations seemed to be known. Surprisingly, in this well-investigated field, a completely new discovery led to the present invention, according to which novel androgens are provided.

Natural steroid hormones, such as testosterone and estradiol, have the configuration 14α and 17β. The invention now resides in the unexpected finding of novel steroids which are characterised by the opposite configuration, viz. 14β,17α. These steroids according to the invention are (14β,17α)-17-(hydroxymethyl) steroids, and they are found to have in common an androgenic activity. A medical use of such compounds has not been known in the art. The compounds only figure in disclosures on intermediates in the partial synthesis of aldosterone, see Barton, D. H. et al, J.Chem.Soc., No. 6 of 1957, 2698–2706 (1957) and Da Silva Campos The invention thus pertains to these steroids for use as a medicine. The invention also pertains to pharmaceutical formulations comprising any or more of such steroids together with pharmaceutically acceptable auxiliaries. A proviso is made in that carbon atom number 11 of the steroid skeleton does not carry, as a substituent, a homocyclic or heterocyclic aryl group. The latter disclaimer is made on the basis of EP 277 676. This disclosure pertains to anti-progestagens having an 11-aryl substituent, which is typical for steroids having that activity. Incidentally, in two examples a mixture of two compounds having different steric configurations is prepared, a component in the mixture being a compound having a 14β,17α configuration.

The above compounds of the invention are well characterised with reference to the requirement that they have a 17-hydroxymethyl group, and that the configuration be 14β and 17α. In other words, the exact nature of any optional substituents at any carbon atom of the steroid skeleton, or at any subsituent group, is not particularly critical to the invention. The person of ordinary skill in the art of steroid chemistry is well aware of which substituents are practically applicable.

It should be noted that in the past steroids having the abnormal 14β,17α configuration received some attention in the art of organic chemistry. See e.g. the more than thirty year old publication of Crabbé, P. et al, Can. J. Chem. 46, 349 (1968). This document incidentally mentions one (14β,17α)-17-(hydroxymethyl) steroid, viz. 20-hydroxy-14β,17α-19-norpregn-4-en-3-one as a chemical intermediate. Similarly, other (14β,17α)-17-(hydroxymethyl) steroids known as chemical compounds per se, are (3β,5α,14β,17α)-pregna-3,20-diol and (3β,14β,17α)-pregna-5,9(11)-diene-3,20-diol, see Shoppee C W et al, Helv. Chim. Acta, 27, 246 (1944) and J. Chem. Soc., 3610 (1962), and (14β,17α)-20-hydroxy-19-norpregn-4-en-3-one, see Crabbe P et al, Can. J. Chem., 46, 349 (1968). To the extent that the invention pertains to chemical compounds, these known compounds are disclaimed here. This also holds for 5α,14β,17α-pregnane-3β,17,20-triol 3,20-diacetate (Chem. Pharm. Bull. vol. 16 Nov. 11, 1968, pages 2223–2227).

The invention particularly pertains to steroids which satisfy structural formula I given below, or pharmaceutically acceptable salts or esters, prodrugs and precursors thereof.

Formula I

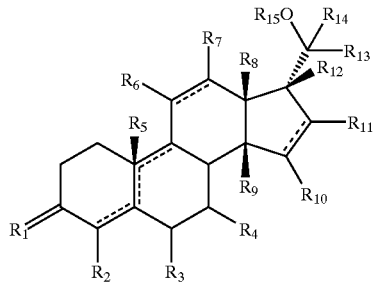

wherein $R_1$ is O, (H,H), (H,OR), NOR, with R being hydrogen, $(C_{1-6})$alkyl $(C_{1-6})$acyl;

$R_2$ is hydrogen, $(C_{1-6})$alkyl, or halogen;

$R_3$ is hydrogen, $(C_{1-6})$alky, $(C_{2-6})$alkenyl, or $(C_{2-6})$alkynyl;

$R_4$ is hydrogen, halogen, or cyano; or $R_4$ is $(C_{1-6})$alky, $(C_{2-6})$alkenyl or $(C_26)$ alkynyl, each optionally substituted by hydroxy, $(C_{1-4})$alkoxy, oxo, halogen, or cyano;

$R_5$ is hydrogen, or $(C_{1-6})$alkyl;

$R_6$ is hydrogen, $(C_{1-6})$alkoxy, or halogen; or $R_6$ is $(C_{1-6})$alkyl, $(C_{2-6})$alkenyl, $(C_{2-6})$alkynyl, a $(C_{1-6})$alkylidene group, or a $(C_{2-6})$alkenylidene group, each optionally substituted by hydroxy, $(C_{1-4})$alkoxy, oxo, halogen, or cyano;

$R_7$ is hydrogen, or $(C_{1-6})$alkyl;

$R_8$ is $(C_{1-6})$alkyl;

$R_9$ is hydrogen, halogen or cyano; or $R_9$ is $(C_{1-6})$alkyl, $(C_{2-6})$alkenyl, or $(C_{2-6})$alkynyl, each optionally substituted by hydroxy, $(C_{1-4})$alkoxy, oxo, halogen, or cyano;

$R_{10}$ is hydrogen, $(C_{1-6})$alkoxy, halogen, or cyano; or $R_{10}$ is $(C_{1-6})$alkyl, $(C_{2-6})$alkenyl or $(C_{2-6})$alkynyl, each optionally substituted by hydroxy, $(C_{1-4})$alkoxy, oxo, halogen, or cyano; or $R_{10}$ together with $R_{11}$ and the carbon atoms at which they are placed form a cyclopropane ring;

$R_{11}$ is hydrogen, $(C_{1-6})$alkoxy, halogen, or cyano; or $R_{11}$ is $(C_{1-6})$alky, $(C_{2-6})$alkenyl or $(C_{2-6})$alkynyl, each optionally substituted by hydroxy, $(C_{1-4})$alkoxy, oxo, halogen, or cyano; or $R_{11}$ together with $R_{10}$ and the carbon atoms at which they are placed form a cyclopropane ring;

$R_{12}$ is hydrogen, hydroxy, halogen, or cyano; or $R_{12}$ is $(C_{1-6})$alkyl, $(C_{2-6})$alkenyl, $(C_{2-6})$alkynyl, each optionally substituted by hydroxy, $(C_{1-4})$alkoxy, oxo, halogen, or cyano;

$R_{13}$ and $R_{14}$ are independently hydrogen, cyano, or phenyl, the latter optionally substituted by hydroxy, $(C_{1-4})$alkoxy, $(C_{1-4})$alkyl or halogen; or $R_{13}$ and $R_{14}$ are independently $(C_{1-6})$alkyl, $C_{2-6})$alkenyl, $(C_{3-6})$ cycloalkyl, $(C_{1-6})$cycloalkenyl or $(C_{2-6})$ alkynyl, each optionally substituted by hydroxy, $(C_{1-4})$alkoxy, phenyl, oxo, halogen, or cyano; or $R_{13}$ and $R_{14}$ together with the carbon atom at which they are placed form a $(C_{3-6})$cycloalkane ring or a $(C_{5-6})$cycloalkene ring;

$R_{15}$ is hydrogen, $SO_3H$, $(C_{1-6})$alkyl, $(C_{1-5})$acyl; and the dotted lines indicate optional bonds.

The term $(C_{1-6})$alkyl as used in the definition of formula I means a branched or unbranched alkyl group having 1–6 carbon atoms, like methyl, ethyl, propyl, isopropyl, butyl, isobutyl, tertiary butyl, pentyl, and hexyl. Likewise, the term $(C_{1-4})$alkyl means an alkyl group having 1–4 carbon atoms. Preferred alkyl groups have 1–4 carbon atoms, and most preferred alkyl groups are methyl and ethyl.

The term $(C_{2-6})$alkenyl means a branched or unbranched alkenyl group having at least one double bond and 2–6-carbon atoms. Preferred alkenyl groups have 2–4 carbon atoms, such as vinyl and propenyl.

The term $(C_{2-6})$alkynyl means a branched or unbranched alkynyl group having at least one triple bond and 2–6 carbon atoms. Preferred alkynyl groups have 2–4 carbon atoms, such as ethynyl and propynyl.

The term $(C_{1-6})$alkylidene means a branched or unbranched alkylidene group having 1–6 carbon atoms. Preferred alkylidene groups have 1–4 carbon atoms, and most preferred is methylene.

The term $(C_{2-6})$alkenylidene means a branched or unbranched alkenylidene group having 2–6 carbon atoms. Preferred alkenylidene groups have 2–4 carbon atoms, such as ethenylidene.

The term $(C_{3-6})$cycloalkyl or $(C_{3-6})$cycloalkane ring means a cycloalkane ring having 3–6 carbon atoms, like cyclopropane, cyclobutane, cyclopentane and cyclohexane.

The term $(C_{5-6})$cycloalkenyl or $(C_{5-6})$cycloalkene ring means a cycloalkene ring having at least one double bond and 5 or 6 carbon atoms.

The term $(C_{1-6})$alkoxy means a branched or unbranched alkyloxy group having 1–6 carbon atoms, like methyloxy, ethyloxy, propyloxy, isopropyloxy, butyloxy, isobutyloxy, tertiary butyloxy, pentyloxy, and hexyloxy. Likewise, the term $(C_{1-4})$alkoxy means a branched or unbranched alkyloxy group having 1–4 carbon atoms. Preferred alkyloxy groups have 1–4 carbon atoms, and most preferred is methyloxy.

The term $(C_{1-15})$acyl means an acyl group derived from a carboxylic acid having from 1–15 carbon atoms, like formyl, acetyl, propanoyl, butyryl, 2-methylpropanoyl, pentanoyl, pivaloyl, hexanoyl, and so on. Also included within the definition of $(C_{1-15})$acyl are [$(C_{3-6})$cycloalkyl]carbonyl,

[$(C_{5-6})$cycloalkenyl]carbonyl, benzoyl,
[[$(C_{1-12})$alkyl]($C_{3-6}$)cycloalkyl]carbonyl,
[[$(C_{2-12})$alkenyl]($C_{3-6}$)cycloalkyl]carbonyl],
[[$(C_{2-12})$alkynyl]($C_{3-6}$)cycloalkyl]carbonyl],
[[$(C_{1-10})$alkyl]($C_{5-6}$)cycloalkenyl]carbonyl],
[[$(C_{2-10})$alkenyl]($C_{5-6}$)cycloalkenyl]carbonyl],
[[$(C_{2-10})$alkynyl]($C_{1-6}$)cycloalkenyl]carbonyl],
$(C_{1-9})$alkylbenzoyl,
$(C_{2-9})$alkenylbenzoyl,
$(C_{2-9})$alkynylbenzoyl.

Also included within the definition of $(C_{1-15})$acyl are acyl groups derived from dicarboxylic acids, like hemi-maloyl, hemi-succinoyl, hemi-glutaroyl, and so on. Preferred is hemi-succinoyl.

The term halogen means fluorine, chlorine, bromine, or iodine. When halogen is a substituent at an alkyl group, like in the definition $R_2$, $R_4$, $R_6$, $R_{9-14}$, Cl and F are preferred, F being most preferred.

It is understood that the (14β,17α)-17-(hydroxymethyl) steroid derivatives of the invention have the natural configurations 5α, 8β, 9α, 10β, 13β.

The (14β,17α)-17-(hydroxymethyl) steroid derivatives of this invention have the natural configurations 5α, 8β, 9α, 10β, 13β, and possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

For therapeutic use, salts of the compounds of formula I are those wherein the counterion is pharmaceutically acceptable. However, salts of the acids according to formula I [i.e. compounds wherein $R_1$ is (H,OSO$_3$H) or wherein $R_{15}$ is SO$_3$H] may also find use, for example, in the preparation or purification of a pharmaceutically acceptable compound. All salts, whether pharmaceutically acceptable or not, are included within the ambit of the present invention. Examples of salts of acids according to the invention are mineral salts such as sodium salt, potassium salt, and salts derived from organic bases like ammonia, imidazole, ethylenediamine, triethylamine and the like.

The compounds of the invention as described hereinbefore in general possess an unexpected androgenic activity. Androgenic activity can be measured in various ways. Thus, the potency of androgens can be determined in vitro using the cytoplasmic androgen receptor from human breast tumor cells (MCF-7 cell line); see Bergink, E. W. et al, Comparison of the receptor binding properties of nandrolone and testosterone under in vitro and in vivo conditions, J. Steroid Biochem. 22, 831–836 (1985). It is also possible to use Chinese hamster ovary (CHO) cells transfected with the human androgen receptor (incubation time 16 h, temperature 4° C.) and compared with the affinity of 5α-dihydrotestosterone [according to the procedure described by Bergink, E. W. et al, J. Steroid Biochem. 12, 1563–1570 (1983)]. The transactivative androgen activity of the compounds of the invention can be measured, e.g. in Chinese hamster ovary cells (CHO) transfected with the human androgen receptor (hAR), in combination with a mouse mammary tumor virus (MMTV), and luciferase receptor gene (incubation time 16 h, temperature 37° C.) and compared with the activity of 5α-dihydrotestosterone [according to the procedure described by Schoonen, W. G. E. J. et al, Analyt. Biochem. 261, 222–224 (1998)]. For the in vivo potency determination of androgens the classical Hershberger test can be used. In this test the androgenic (increase in prostate weight) and anabolic activities [increase of the musculus levator ani (MLA)] of a compound are tested in immature castrated rats after daily administration for 7 days; see Hershberger, L. G. et al, Myotrophic activity of 19-Nortestosterone and other steroids determined by modified levator ani muscle method, Proceedings of the society for experimental biology and medicine 83, 175–180 (1953). Additionally, the effect of an androgenic compound on LH suppression can be tested in mature castrated rats according to Kumar, N. et al, The biological activity of 7alpha-methyl-19-nortestosterone is not amplified in male reproductive tract as is that of testosterone, Endocrinology 130, 3677–3683 (1992).

The preference goes to those compounds according to the invention which exhibit a relatively high androgenic activity. Thus, the preferred compounds of the invention are those satisfying the above structural formula I, wherein:

$R_1$ is O;
$R_2$, $R_3$, $R_5$, $R_6$, $R_7$, $R_9$, $R_{10}$, $R_{11}$, $R_{12}$, and $R_{14}$ all are hydrogen;
$R_4$ is H or methyl;
$R_8$ is methyl;
$R_{13}$ is hydrogen, or $C_{1-2}$(alkyl) with the configuration at carbon atom no. 20 being S;
$R_{15}$ is H or $(C_{1-15})$acyl;
and wherein a double bond is present between carbon atoms nos. 4 and 5, and optionally also between carbon atoms nos. 9 and 10.

As androgenic hormones the (14β,17α)-17-(hydroxymethyl) steroids of the present invention can be used in, int.al., male contraception and male HRT (hormone replacement therapy). Thus, e.g. male contraception may comprise a regimen of administration of hormones in which a progestagen serves to achieve a contraceptive effect and an androgen serves to supplement the resulting decreased testosterone level. Another option is that male contraception is performed with an androgenic hormone alone. The androgens can also be used for androgen supplementation in the partially androgen deficient ageing male. Next to the use in the male, the androgens of the invention also can be used in the female, e.g. as androgen replacement therapy in postmenopausal women.

The present invention also relates to a pharmaceutical composition comprising a steroid compound according to the invention mixed with a pharmaceutically acceptable auxiliary, such as described in the standard reference, Gennaro et al, *Remmington's Pharmaceutical Sciences*, (18th ed., Mack Publishing Company, 1990, see especially Part 8: Pharmaceutical Preparations and Their Manufacture). The mixture of the steroid compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The steroid compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the steroid compound according to the invention for the manufacture of a medicament in the treatment of androgen-deficiency, such as in male or female HRT (hormone replacement therapy). Accordingly, the invention also includes a method of treatment in the field of male or female HRT, comprising the administration to a male or female patient suffering from an androgen-deficiency, of a compound as described hereinbefore (in a suitable pharmaceutical dosage form).

Further, the invention relates to the use of a steroid compound according to the invention for the manufacture of a medicament having contraceptive activity (for which in the art the term "contraceptive agent" is also used). Thus the invention also pertains to the medical indication of contraception, i.e. a method of contraception comprising the administration to a subject, being a male, preferably a human male, of a compound as described hereinbefore (in a suitable pharmaceutical dosage form), in combined therapy with a progestagen or not.

The androgens according to the invention can also be used in a kit for male contraception. Although this kit can comprise one or more androgens only, it is preferred that it comprises means for the administration of a progestagen and means for the administration of an androgen. The latter means is a pharmaceutical formulation comprising compound according to the invention as described hereinbefore, and a pharmaceutically acceptable carrier.

The invention also pertains to a method of treatment comprising administering to a (notably human) male or female in need of androgen-supplementation a therapeutically effective amount of a (14β,17α)-17-(hydroxymethyl) steroid as described hereinbefore. This is irrespective of whether or not the need for androgen-supplementation has arisen as a result of male contraception involving the administration of a sterilitant, such as a progestagen.

Further, the invention pertains to a method of contraception, comprising administering to a fertile male, notably human, a (14β,17α)-17-(hydroxymethyl) steroid as described hereinbefore in a dosage amount and regimen which is sufficient for said compound to be contraceptively effective per se. Alternatively, the method of contraception provided by the present invention comprises administering to a fertile male, notably human, a contraceptively effective combination of a sterilitant, such as a progestagen, and a (14β,17α)-17-(hydroxymethyl) steroid as described hereinbefore.

The compounds of the invention may be produced by various methods known in the art of organic chemistry in general, and especially in the art of the chemistry of steroids (see, for example: Fried, J. et al, *Organic Reactions in Steroid Chemistry*, Volumes I and II, Van Nostrand Reinhold Company, New York, 1972).

Crucial is the synthesis of steroids of inverted stereochemistry at C-14 (14β-configuration) and possessing a (substituted) 17α-hydroxymethyl group.

A convenient starting material for the preparation of compounds of formula I wherein $R_1$ is oxo; $R_2$, $R_5$, $R_9$, $R_{10}$, $R_{11}$, $R_{12}$ and $R_{15}$ are hydrogen; $R_3$, $R_4$, $R_6$ and $R_7$ are hydrogen or $(C_{1-6})$ alkyl; $R_8$ is methyl; $R_{13}$ and $R_{14}$ have the previously given meaning; and the dotted lines indicate a $\Delta^4$ double bond, is for instance a compound of general formula II, wherein $R_3$, $R_4$, $R_6$ and $R_7$ are hydrogen or $(C_{1-6})$alkyl, whose synthesis is known in literature, or which can be prepared using standard methods.

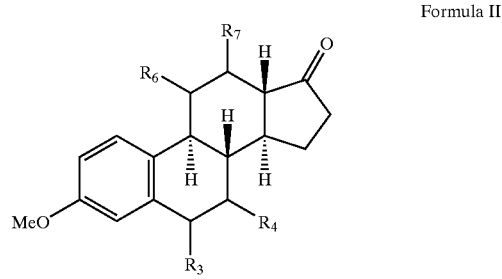

Formula II

A possible synthesis route starts with the transformation of compounds of formula II to the corresponding 14β-derivatives. A 3-methoxyestra-1,3,5(10)-trien-17-one can be converted to a cyclic 1,2-ethanediyl acetal which can then be brominated to afford a (16α)-16-bromo-3-methoxyestra-1, 3,5(10)-trien-17-one cyclic 1,2-ethanediyl acetal derivative. Bromination can be accomplished using pyridinium tribromide, phenyltrimethylammonium tribromide or other brominating agents known in the art [Rasmusson, G. H. et al, Steroids 22, 107 (1973)]. The 16α-bromo compound is dehydrobrominated by reaction with a base, e.g. potassium tert-butoxide in xylene or dimethyl sulfoxide, to give the $\Delta^{15}$ compound [Johnson, W. S. et al, J. Am. Chem. Soc. 79, 2005 (1957); Poirier, D. et al, Tetrahedron 47, 7751 (1991)]. Mild hydrolysis of the ethylene ketal, for instance by treatment with p-toluenesulfonic acid in a mixture of acetone and water [Johnson, supra], results in a 3-methoxyestra-1,3,5 (10),15-tetraen-17-one derivative which is then converted to a 3-methoxyestra-1,3,5(10),14,16-pentaen-17-ol acetate by acid-catalyzed reaction with acetic anhydride, isopropenyl acetate or other acetylating agents [Rasmusson, supra; Bull, J. R. et al, J. Chem. Soc., Perkin Trans. 1, 241 (1990)]. The acetate is treated with sodium borohydride or other reducing agents [Rasmusson, supra] to result in the formation of a (17β)-3-methoxyestra-1,3,5(10),14-tetraen-17-ol derivative. The $\Delta^{14}$ double bond is hydrogenated, for instance by using palladium on activated carbon [Schubert, G. et al, Z. Chem. 23, 410 (1983)], whereafter oxidation of the resulting (14β,17β)-3-methoxyestra-1,3,5(10)-trien-17-ol derivative results in the formation of a (14β)-3-methoxyestra-1,3,5 (10)-trien-17-one derivative (for oxidations, see Hudlicky, M., *Oxidations in Organic Chemistry*, ACS Monograph 186, Washington, D.C., 1990). A 3-methoxyestra-1,3,5(10),15-tetraen-17-one derivative can also be subjected to acid-catalyzed isomerization to produce a mixture of (14β)-3-methoxyestra-1,3,5(10),15-tetraen-17-one and 3-methoxyestra-1,3,5(10),14-tetraen-derivatives which can be hydrogenated as described above to a (14β)-3-methoxyestra-1,3,5(10)-trien-17-one derivative. Alternatively, they can be separated after which the (14β)-3-methoxyestra-1,3,5(10),15-tetraen-17-one derivative can be converted by 1,4-reduction to the (14β)-3-methoxyestra-1,3,5(10)-trien-17-one. A (14β)-3-methoxyestra-1,3,5(10)-trien-17-one derivative can also be optained as follows: a 3-methoxyestra-1,3,5(10)-trien-17-one derivative is brominated directly, for instance by reaction with copper(II) bromide in benzene/methanol [Segaloff, A. el al, Steroids 22, 99 (1973)], or by reaction of the corresponding enol acetate with bromine [Johnson, supra], to produce a 16α-bromoketone derivative. Dehydrobromination, e.g. by reaction with LiBr/Li$_2$CO$_3$/DMF [Bull, supra], usually results in a mixture of (14β)-3-methoxyestra-1,3,5(10),15-tetraen-17-one and 3-methoxyestra-1,3,5(10),14-tetraen-17-one derivatives which can be processed as described above.

Alternative methods to introduce a $\Delta^{15}$ double bond include: conversion of a 3-methoxyestra-1,3,5(10)-trien-17-one to the corresponding enol silyl ether or enol acetate and reaction with a palladium(II) salt [Bull, J. R. et al, J. Chem. Soc., Perkin Trans. I, 1269 (1996); Takahashi, T. et al, Tetrahedron 41, 5747 (1985)] or reaction of the enolate with methyl 2-pyridinesulfinate [Dionne, P. et al, Steroids 62, 674 (1997)].

A (14β)-3-methoxyestra-1,3,5(10)-trien-17-one derivative thus obtained can now be converted to a (14β,17α)-3-methoxyestra-1,3,5(10)-triene-17-methanol derivative. The conversion of 17-oxo to 17α-CH$_2$OH can be accomplished in several ways:

(a) 1: Wittig or Peterson reaction to a (14β)-3-methoxy-17-methyleneestra-1,3,5(10)-triene derivative [Maercker, A., in Org. Reactions 14, p. 270, Wiley, New York, 1965; Ager, D. J., in Org. Reactions 38, p. 1, Wiley, New York, 1990]; 2: hydroboration, for instance by use of 9-BBN, disiamylborane, or thexylborane [see e.g. Zweifel, G. et al, in Org. Reactions S, p. 1, Wiley, New York, 1963], resulting in the formation of a (14β17α)-3-methoxyestra-1,3,5(10)-triene-17-methanol derivative.

(b) 1: Conversion of the 17-ketone to a (14β,17α)-3-methoxyspiroestra-1,3,5(10)-triene[17,2']oxirane by reaction with e.g. trimethylsulfonium iodide/n-BuLi [Corey, E. J. et al, J. Am. Chem. Soc. 87, 1353 (1965)]; 2: (Lewis) acid-catalyzed isomerization of the 17α-oxirane to 17α-formyl [Rickborn, B., in Comprehensive Organic Synthesis, Vol. 3, p. 733, Pergamon Press, Oxford, N.Y. (1991)]; 3: reduction of 17α-fornyl to 17α-CH$_2$OH.

(c) 1: Conversion of the 17-ketone to a 17-methylene compound; 2: epoxidation with e.g. a peroxy acid, such as n'-chloroperberzoic acid, to a (14β,17α)- and/or (14β17β)-3-methoxyspiroestra-1,3,5(10)-triene[17,2']oxirane; 3: (Lewis)acid-catalyzed isomerization of the 17-oxirane to 17-formyl as described under (b); 4: reduction of 17-formyl to 17-CH$_2$OH.

(d) 1: Conversion of the 17-ketone to a 17α- or 17β-oxirane as described under (b) and (c); 2: Lewis acid-catalyzed reduction to the 17-methanol steroid [using e.g. NaBH$_3$CN/BF$_3$.Et$_2$O, see: Tone, H. et al, Tetrahedron Lett. 28, 4569 (1987)].

(e) 1: Reaction of the 17-ketone to the 17-cyano steroid by reaction with tosylmethyl isocyanide [TosMIC, see Bull, J. R. et al, Tetrahedron 31, 2151 (1975)]; 2: reduction of the cyano group to formyl by diisobutylaluminum hydride; 3: reduction of the 17-formyl group to 17-CH$_2$OH.

(f) 1: Wittig condensation with (Ph)$_3$P=CHOMe; 2: hydrolysis of the resulting enol ether; 3: reduction of 17-formyl to 17-CH$_2$OH.

(g) 1: Conversion of the 17-ketone to a 17α- or 17β-oxirane as described under (b) and (c); 2: elimination to a (14β)-3-methoxyestra-1,3,5(10),16-tetraene-17-methanol derivative; 3: hydrogenation of the $\Delta^{16}$ double bond.

(h) 1: Conversion of the 17-ketone to the corresponding enol triflate [see e.g. Cacchi, S. et al, Tetrahedron Lett. 25, 4821 (1984)]; 2: palladium-catalyzed alkoxycarbonylation of the latter to a alkyl (14β)-3-methoxyestra-1,3,5(10),16-tetraene-17-carboxylate [Cacchi, S. et al, Tetrahedron Lett. 26, 1109 (1985)]; 3: reduction of the latter to the corresponding (14β)-3-methoxyestra-1,3,5(10),16-tetraene-17-methanol derivative; 4: hydrogenation of the $\Delta^{16}$ double bond.

(i) 1: Conversion of the 17-ketone to a alkyl (14β)-3-methoxyestra-1,3,5(10),16-tetraene-17-carboxylate as described under (h); 2: 1,4-reduction, e.g. by hydrogenation or by lithium or sodium in liquid ammonia, to a alkyl (14β,17α)-3-methoxyestra-1,3,5(10)-triene-17-carboxylate derivative; 3: reduction of the ester to 17-CH$_2$OH.

Some of these methods (a,b,c,e,g) result in the stereoselective formation of the 17α-CH$_2$OH isomer. Others (d,f,h,i) may give mixtures which can be separated by chromatography or crystallization.

Birch reduction of the (14β,17α)-3-methoxyestra-1,3,5(10)-triene-17-methanol derivatives thus obtained [Caine, D. in Org. Reactions 23, p. 1, Wiley, New York, 1976] and hydrolysis of the resulting (14β,17α)-3-methoxyestra-2,5(10)-diene-17-methanol derivative then provides a (14β,17α)-17-(hydroxymethyl)estr-4-en-3-one derivative of the invention.

Optionally, a (14β,17α)-3-methoxyestra-1,3,5(10)-triene-17-methanol derivative can be oxidized as described above to the corresponding 17-carboxaldehyde. The aldehyde can be reacted with an (organometallic) compound of formula R$_{13}$M in which R$_{13}$ has the previously given meaning except for hydrogen, any functional groups present in R$_{13}$ being suitably protected, and M is Li, Na, K, MgX, ZnX, CeX$_2$, SiR$_3$ or SnR$_3$, to produce a (14β,17α)-3-methoxy-17-(CHR$_{13}$OH)estra-1,3,5(10)-triene which is usually a mixture of C-20 epimers. The latter can be separated whereafter Birch reduction and hydrolysis as described above and removal of any protecting groups still present provides the (14β,17α)-17-(CHR$_{13}$OH)estr-4-en-3-one derivatives of the invention in which R$_{13}$ has the previously given meaning except for hydrogen.

Optionally, a (14β,17α)-3-methoxy-17-(CHR$_{13}$OH)estra-1,3,5(10)-triene can be oxidized as described above to obtain a 20-ketone which can then be reacted with an (organometallic) compound of formula R$_{14}$M, R$_{14}$ having the previously given meaning except for hydrogen, any functional groups present in $R_{14}$ being suitably protected, and M having the previously given meaning. In that case Birch reduction, hydrolysis and removal of any protecting groups still present will provide (14β,17α)-17-($CR_{13}R_{14}OH$)estr-4-en-3-one derivatives of the invention wherein $R_{13}$ and $R_{14}$ have the previously given meaning except for hydrogen. This procedure can also be used for the preparation of compounds of the invention in which $R_{13}$ and $R_{14}$ together with the carbon atom at which they are placed form a ($C_{3-6}$)cycloalkyl ring or a ($C_{5-6}$)cycloalkenyl ring.

Optionally, the 20-ketone can be reduced by reaction with $LiAlH_4$, $NABH_4$ or other reducing agents. In that case, (14β,17α)-17-($CHR_{13}OH$)estr-4-en-3-one derivatives are obtained of inverted stereochemistry at C-20.

Optionally, a (14β,17α)-3-methoxyestra-2,5(10)-diene-17-methanol derivative, i.e. the product obtained after the Birch reduction, can be oxidized as described above to the corresponding 17-carboxaldehyde. Reaction with a compound of formula $R_{13}M$ as described above and hydrolysis affords the (14β,17α)-17-($CHR_{13}OH$)estr-4-en-3-one derivatives of the invention as already described above. This reaction sequence allows the introduction of substituents $R_{13}$, and analogously, $R_{14}$, which would not survive a Birch reduction. Optionally, the (14β,17α)-3-methoxyestra-2,5 (10)-diene-17-methanol derivative might also be converted to a more stable system, e.g. a (14β,17α)-3,3-dimethoxyestr-5(10)-ene-17-methanol derivative or a (14β,17α)-17-(hydroxymethyl)estr-4-en-3-one cyclic 1,2-ethanediyl (dithio)acetal derivative, prior to oxidation and reaction with $R_{13}M$, and so on.

Wittig reaction of a (14β)-3-methoxyestra-1,3,5(10)-trien-17-one derivative with e.g. ethyltriphenylphosphonium bromide leads predominantly to the (17Z)-ethylidene derivative which on hydroboration gives the (14β,17α,20R)-3-methoxy-19-norpregna-1,3,5(10)-trien-20-ol derivative. Birch reduction and hydrolysis then results in (14β17α,20R)-20-hydroxy-19-norpregn-4-en-3-one derivatives of the invention ($R_{13}=CH_3$). On the other hand, Wittig-Horner reaction with e.g. triethyl phosphonoacetate results in a ethyl (14β,17E)-3-methoxy-19-norpregna-1,3,5(10),17(20)-tetraen-21-oate, which can be converted, by methods known in the art to a (14β,17E)-3-methoxy-19-norpregna-1,3,5(10),17(20)-tetraene, which on hydroboration results in a (14β,17α,20S)-3-methoxy-19-norpregna-1,3,5(10)-trien-20-ol derivative. Optionally, the ethyl (14β,17E)-3-methoxy-19-norpregna-1,3,5(10),17(20)-tetraen-21-oate can be subjected to homologation, by using methods known in the art, prior to hydroboration to the 20-hydroxy compound, which provides an additional method to obtain a (14β,17α,20S)-17-($CHR_{13}OH$)estr-4-en-3-one derivative of the invention in which $R_{13}$ has the previously given meaning except for hydrogen. Techniques for homologation are known in the art [Mathieu, J. et al: *Formation of C-C Bonds*, Vol. I–III, Georg Thieme Publishers, Stuttgart, 1973].

Compounds of formula I with substituents at C-3, C-4, C-6, C-7, C-10, C-11, C-13, C-14, C-15, C-16 and C-17 other than those described under the definition of formula II, or compounds without double bonds in the steroid nucleus or with double bonds other than a $\Delta^{14}$ double bond, can be prepared as follows.

Compounds of the invention in which $R_1$ is (H,H), (H,OR), NOR, and R is H, ($C_{1-6}$)alkyl, or ($C_{1-6}$)acyl can be prepared, using standard methods, from compounds of formula I in which $R_1$ is oxo.

Compounds in which $R_2$ is ($C_{1-6}$)alkyl or halogen are obtained, using standard methods, from compounds of formula I in which $R_2$ is hydrogen.

Compounds in which $R_3$ is ($C_{2-6}$)alkenyl or ($C_{2-6}$)alkynyl are obtained, using standard methods, from compounds of formula I in which $R_3$ is hydrogen.

Compounds in which $R_4$ has the meaning described above except for hydrogen or ($C_{1-6}$)alkyl can be prepared from e.g. (7α,17β)-7-ethenyl-17-hydroxyestr-4-en-3-one which can be prepared by copper(I)-catalyzed 1,6-addition of vinyllithium or a vinylmagnesium compound to e.g. (17β)-17-(acetyloxy)estra-4,6-dien-3-one [Syntex, DE 1143199 (1963)]. Conversion to (7α)-7-ethenyl-3-methoxyestra-1,3,5(10)-trien-17-one and construction of the functionalized and/or unsaturated side-chain at C-7 from 7-ethenyl are carried out using standard methods. Inversion of the stereochemistry at C-14 and construction of the side-chain at C-17 are carried out as described above. The precise sequence of reaction steps needed for the inversion at C-14 and for the construction of the two side-chains, including the Birch reduction and the hydrolysis of the resulting estra-2,5(10)-diene, is dictated by methods common in synthetic strategy.

Compounds in which $R_5$ is methyl can be prepared from e.g. (3β)-3-(acetyloxy)androsta-5,14-dien-17-one [Andre, A. F. St. et al, J. Am. Chem. Soc. 74, 5506 (1952)].

Compounds in which $R_6$ has the previously given meaning except for hydrogen or ($C_{1-6}$)alkyl can be obtained from e.g. (11α)-11-hydroxy-3-methoxyestra-1,3,5(10)-trien-17-one cyclic 1,2-ethanediyl acetal [Collins, D. J. et al, Aust. J. Chem. 3, 339 (1983)], (11β)-11-hydroxy-3-methoxyestra-1,3,5(10)-trien-17-one cyclic 1,2-ethanediyl acetal [Choe, Y. S. et al, J. Med. Chem. 38, 816 (1995)], (11β)-11-(hydroxymethyl)-3-methoxyestra-1,3,5(10)-trien-17-one cyclic 1,2-ethanediyl acetal [van den Broek, A. J. et al, Steroids 30, 481 (1977)], or 3-methoxyestra-1,3,5(10)-triene-11,17-dione cyclic 17-(1,2-ethanediyl acetal) [van den Broek, A. J. et al, Recl. Trav. Chim. Pays-Bas 94, 35 (1975)]. The precise sequence of reaction steps needed for the construction of 11-substituted compounds of the invention is again dictated by methods common in synthetic strategy.

Compounds in which $R_8$ is ethyl can be prepared from e.g. 13-ethylgon-4-ene-3,17-dione [Brito, M. et al, Synth. Comm. 26, 623 (1996)].

14β-Substituted compounds can be obtained by a slight modification of a method described by Bull which enables the conversion of a (17β)-3-methoxyestra-1,3,5(10),14-tetraen-17-ol derivative to 14-substituted (14β)-3-methoxyestra-1,3,5(10)-trien-17-one compounds [Bull, J. R. et al, J. Chem. Soc., Perkin Trans. I, 37 (1987)]. The latter can be converted to the compounds of the invention by methods described above.

15-Substituted compounds can be obtained as follows. Conjugated addition of an (organometallic) compound of formula $R_{10}M$ wherein $R_{10}$ has the previously given meaning, any functional groups present in $R_{10}$ being suitably protected, and M having the previously given meaning, to a (14β)-3-methoxyestra-1,3,5(10),15-tetraen-17-one derivative provides a (14β)-3-methoxyestra-1,3,5(10)-trien-17-one derivative, substituted at C-15, which can then be converted as described above to a (14β,17α)-17-(hydroxymethyl)estr-4-en-3-one derivative of the invention, substituted at C-15.

16-Substituted compounds can be obtained via alkylation at C-16 of a (14β)-3-methoxyestra-1,3,5(10)-trien-17-one derivative, usually resulting in the predominant formation of the 16β-isomer. Optionally, the stereochemistry at C-16 can be inverted by deprotonation followed by hydrolysis.

15,16-Methylene derivatives can be obtained from a (14β)-3-methoxyestra-1,3,5(10),15-tetraen-17-one by reaction with trimethyl sulfoxonium iodide/base to produce a (14β,15β,16β)-3-methoxy-15,16-methyleneestra-1,3,5(10)-trien-17-one which is processed as described above.

17β-Substituted compounds of formula I can be obtained via alkylation of a alkyl (14β,17α)-3-methoxyestra-1,3,5 (10)-triene-17-carboxylate.

Compounds of the invention in which $R_{15}$ is $SO_3H$, $(C_{1-6})$alkyl, $(C_{1-15})$acyl are obtained, by using methods known in the art, from compounds of formula I in which $R_{15}$ is hydrogen.

Compounds of the invention without unsaturations in the steroid nucleus are produced from $\Delta^4$ compounds wherein $R_1$ is oxo.

Compounds of the invention having a $\Delta^5(10)$ double bond, or a $\Delta^{4,9}$ diene system are produced from the $\Delta^{2,5}(10)$ dienes obtained after the Birch reduction.

Compounds having a $\Delta^{11}$ double bond can be prepared from e.g. estra-4,11-diene-3,17-dione [Broess, A. I. A. et al, Steroids 57, 514 (1992)].

Compounds of the invention having a $\Delta^{15}$ double bond can be prepared from a (14β)-3-methoxyestra-1,3,5(10),16-tetraene-17-methanol derivative by the sequence: protection of the hydroxy group, e.g. as a tert-butyldimethylsilyl ether; hydroboration of the $\Delta^{16}$ double bond to produce a (14β,16β,17α)-17-[[[(1,1-dimethylethyl)dimethylsilyl]oxy]methyl]-3-methoxyestra-1,3,5(10)trien-16-ol, oxidation to the corresponding 16-ketone, conversion of 16-oxo to a $\Delta^{15}$ double bond, and finally, Birch reduction/hydrolysis.

The invention will be further explained hereinafter with reference to the following Examples.

1) UNSUBSTITUTED COMPOUNDS

EXAMPLE 1

(14β,17α)-17-(Hydroxymethyl)estr-4-en-3-one i)—Lithium amide (6.6 g) was added to a suspension of methyltriphenylphosphonium bromide (113 g) in dry toluene (300 ml) and dry dimethyl sulfoxide (24 ml). The reaction mixture was heated to 65° C. for 30 min. After cooling to 35–40° C., a solution of (14β)-3-methoxyestra-1,3,5(10)-trien-17-one [Johnson, W. S. et al, J. Am. Chem. Soc. 79, 2005 (1957); 30 g] in dry toluene (225 ml) was added and the mixture was heated at 60° C. for 22 h. Then it was cooled and poured into water. The product was extracted into ethyl acetate; the combined organic phases were dried over sodium sulfate and concentrated under reduced pressure. In order to achieve complete conversion of starting material, the procedure was repeated. The triphenylphosphine oxide was removed by addition of diethyl ether and filtration. Column chromatography of the crude product afforded (14β)-3-methoxy-17-methyleneestra-1,3,5 (10)-triene (26 g).

ii)—A solution of borane-dimethyl sulfide complex (26.6 ml) in dry tetrahydrofuran (105 ml) was cooled to 0° C. A solution of 1,5-cyclooctadiene (33 ml) in dry tetrahydrofuran (32 ml) was added dropwise in 45 min. while maintaining the temperature below 10° C. The mixture was heated under reflux for 1 h and then cooled to 13° C. A solution of the product obtained in the previous step (25 g) in dry tetrahydrofuran (100 ml) was added in 10 min. and the reaction mixture was heated under reflux for 2.5 h and then stirred at room temperature overnight. An aqueous solution of sodium hydroxide (3 M, 120 ml) was added in 30 min., followed by an aqueous solution of hydrogen peroxide (30%, 120 ml) in 1 h (T≦50° C.). After 2 h stirring the reaction mixture was poured into an aqueous solution of sodium sulfite (10%, 1.75 l) and the product was extracted into ethyl acetate. The combined organic phases were washed with water and brine, dried over sodium sulfate and concentrated under reduced pressure. Trituration (ethanol/water 1:1) afforded (14β17α)-3-methoxyestra-1,3,5(10)-triene-17-methanol (23.6 g)

iii)—The alcohol obtained in the previous step (2.0 g) in dry tetrahydrofuran (35 ml) was added to a solution of lithium (0.86 g) in liquid ammonia (52 ml), cooled between −50° C. and −60° C. After 1 h stirring at −50° C. and 1 h at −40° C., dry ethanol was added and the ammonia was allowed to evaporate. Water was added and the product was extracted into ethyl acetate. The combined organic phases were washed with water and brine, dried over sodium sulfate and concentrated under reduced pressure, to give (14β,17α)-3-methoxyestra-2,5(10)-diene-17-methanol (2.13 g). The product was used in the following step without further purification.

iv)—A solution of the diene obtained in the previous step (0.30 g) in acetone (12 ml) was treated with hydrochloric acid (2–6 M, 0.6 ml). After 0.1–2 h stirring at room temperature, the reaction mixture was neutralized with a saturated aqueous solution of sodium hydrogencarbonate, or with an aqueous solution of sodium hydroxide (1 M) followed by addition of a saturated aqueous solution of sodium hydrogencarbonate. Optionally, the acetone was evaporated under reduced pressure. The product was extracted into ethyl acetate; the combined organic phases were washed with a saturated aqueous solution of sodium hydrogencarbonate and with brine, dried over sodium sulfate and concentrated under reduced pressure. Column chromatography and crystallization afforded (14β,17α)-17-(hydroxymethyl)estr-4-en-3-one (0.21 g), m.p. 115–118° C.

EXAMPLE 2

(14β,17α)-17-(Hydroxymethyl)estr-5(10)-en-3-one

A solution of (14β,17α)-3-methoxyestra-2,5(10)-diene-17-methanol (Example 1, step iii; 0.30 g) in a mixture of methanol (3 ml) and tetrahydrofuran (2.1 ml) was treated with a solution of oxalic acid (0.105 g) in water (1.8 ml). After 1.5 h stirring at room temperature, the reaction mixture was poured into water and the product was extracted into ethyl acetate. The combined organic phases were washed with a saturated aqueous solution of sodium hydrogencarbonate and brine, dried over sodium sulfate and concentrated under reduced pressure. Column chromatography afforded (14β,17α)-17-(hydroxymethyl)estr-5(10)-en-3-one (0.20 g), $^1$H NMR δ 3.77 (m, 1H), 3.52 (t, 1H, J=9.0 Hz), 2.74 (m, 2H), 1.09 (s, 3H).

EXAMPLE 3

(14β,17α)-17-(Hydroxymethyl)estra-4,9-dien-3-one

Phenyltrimethylammonium tribromide (2.28 g) was added in small portions and in 10 min. to a solution of (14β,17α)-17-(hydroxymethyl)estr-5(10)en-3-one (Example 2; 1.75 g) in dry pyridine (47 ml). After 1.5 h stirring at room temperature the mixture was poured into ice-water and the product was extracted into ethyl acetate. The combined organic phases were washed with a saturated aqueous solution of sodium thiosulfate, water, a saturated aqueous solution of sodium hydrogencarbonate and brine, dried over sodium sulfate and concentrated under reduced pressure. Column chromatography provided (14β,17α)-17-(hydroxymethyl)estra-4,9-dien-3-one (0.36 g), $[\alpha]_D^{20}$=−241 (c=1, dioxane).

2) 7-SUBSTITUTED COMPOUNDS

EXAMPLE 4

(7α,14β,17α)-17-(Hydroxymethyl)-7-methylestr-4-en-3-one i)—A mixture of (7α,17β)-3-methoxy-7-methylestr-1,3,5(10),14-tetraen-17-ol [Segaloff, et al, Steroids 22, 99 (1973); 86.2 g] and palladium on activated carbon (5%; 34.5 g) in ethanol (578 ml) and dichloromethane (414 ml) was stirred under hydrogen (3 bar) at room temperature for 24 h. The reaction mixture was filtered and the filtrate was concentrated under reduced pressure, to give (7α,14β,17β)-3-methoxy-7-methylestr-1,3,5(10)-trien-17-ol (83.0 g). The product was used in the following step without further purification.

ii)—A solution of the product obtained in the previous step (37.4 g) in acetone (1880 ml) was cooled to 0° C. Jones reagent (8 M, 37.4 ml) was added dropwise while keeping the temperature below 10° C. The reaction mixture was stirred for 30 min. 2-Propanol (21 ml) was added and after 10 min. stirring the mixture was filtered over dicalite. The filtrate was partially concentrated under reduced pressure and the product was extracted into ethyl acetate. The combined organic phases were washed with a saturated aqueous solution of sodium thiosulfate, a saturated aqueous solution of sodium hydrogencarbonate and brine, dried over sodium sulfate and concentrated under reduced pressure, to give (7α,14β)-3-methoxy-7-methylestr-1,3,5(10)-trien-17-one (35.85 g). The product was used in the following step without further purification.

iii)—A mixture of methyltriphenylphosphonium bromide (21.8 g), potassium tert-butoxide (5.7 g) and dry toluene (218 ml) was heated under reflux for 1 h. A solution of the ketone obtained in the previous step (6.07 g) in dry toluene (50 ml) was added dropwise and heating was continued for another 1 h. After cooling, the reaction mixture was poured into water. The product was extracted into ethyl acetate; the combined organic phases were washed with water and brine, dried over sodium sulfate and concentrated under reduced pressure. Column chromatography of the crude product afforded (7α,14β)-3-methoxy-7-methyl-17-methyleneestra-1,3,5(10)-triene (5.85 g).

iv)—A solution of borane-dimethyl sulfide complex (5.94 ml) in dry tetrahydrofuran (27 ml) was cooled to 0° C. A solution of 1,5-cyclooctadiene (7.36 ml) in dry tetrahydrofuran (7 ml) was added dropwise while maintaining the temperature below 10° C. The mixture was heated under reflux for 1 h and then cooled to room temperature. A solution of the product obtained in the previous step (5.85 g) in dry tetrahydrofuran (70 ml) was added dropwise and the reaction mixture was stirred at room temperature for 1 h. The mixture was cooled to 0° C., and an aqueous solution of sodium hydroxide (2 M, 14.75 ml) was added carefully (T≦15° C.), followed by an aqueous solution of hydrogen peroxide (30%, 11.8 ml). After 2 h stirring the reaction mixture was poured into water and the product was extracted into ethyl acetate. The combined organic phases were washed with an aqueous solution of sodium thiosulfate and brine, dried over sodium sulfate and concentrated under reduced pressure. Column chromatography afforded (7α,14β,17α)-3-methoxy-7-methylestr-1,3,5(10)-triene-17-methanol (1.60 g).

v)—The alcohol obtained in the previous step (1.06 g) in dry tetrahydrofuran (15 ml) was added to a refluxing solution of lithium (1.35 g) in liquid ammonia (64 ml). After 4 h stirring, tert-butanol was added and stirring was continued for 30 min. Ethanol was added and the ammonia was allowed to evaporate. The mixture was poured into water and the product was extracted into ethyl acetate. The combined organic phases were washed with brine, dried over sodium sulfate and concentrated under reduced pressure, to give (7α,14β,17α)-3-methoxy-7-methylestr-2,5(10)-diene-17-methanol (0.79 g). The product was used in the following step without further purification.

vi)—Following a procedure analogous to that described under iv of Example 1, the diene obtained in the previous step (0.79 g) was converted to (7α,14β,17α)-17-(hydroxymethyl)-7-methylestr-4-en-3-one (0.36 g), m.p. 157–159° C.

EXAMPLE 5

(7α,14β,17α)-7-(Hydroxymethyl)-7-methylestra-4,15-dien-3-one i)—m-Chloroperbenzoic acid (70–75%, 14.57 g) was added to a solution of (7α,14β)-3-methoxy-7-methyl-17-methyleneestra-1,3,5(10)-triene (Example-4, step iii; 16.05 g) in diethyl ether (642 ml), containing solid sodium hydrogencarbonate (45.5 g). The reaction mixture was stirred at room temperature for 6 h. Additional m-chloroperbenzoic acid (14.57 g) was added and stirring was continued overnight. The reaction was poured into a saturated aqueous solution of sodium thiosulfate and the product was extracted into ethyl acetate. The combined organic phases were washed with brine, dried over sodium sulfate and concentrated under reduced pressure, to give (7α,14β,17β)-3-methoxy-7-methylspiroestra-1,3,5(10)-triene[17,2']oxirane (16.88 g). The product was used in the next step without further purification.

ii)—A solution of the product obtained in the previous step (16.88 g) in dry 2-propanol (844 ml), containing aluminium isopropoxide (46.88 g), was heated under reflux for 3 h. After cooling, a saturated aqueous solution of potassium sodium tartrate tetrahydrate was added and the product was extracted into ethyl acetate. The combined organic phases were washed with brine, dried over sodium sulfate and concentrated under reduced pressure. Column chromatography afforded (7α,14β)-3-methoxy-7-methylestra-1,3,5(10),16-tetraene-17-methanol (8.68 g).

iii)—A solution of the product obtained in the previous step (1.50 g) and imidazole (3.07 g) in dry dichloromethane (9.4 ml) was treated with t-butyldimethylsilyl chloride (1.38 g). After 2 h stirring at room temperature the reaction mixture was poured into a saturated aqueous solution of sodium hydrogencarbonate. The product was extracted into ethyl acetate; the combined organic phases were washed with brine, dried over sodium sulfate and concentrated under reduced pressure, to give (7α,14β)-17-[[[(1,1-dimethylethyl)dimethylsilyl]oxy]methyl]-3-methoxy-7-methylestra-1,3,5(10),16-tetraene (2.54 g). The product was used in the next step without further purification.

iv)—Following a procedure analogous to that described under iv of Example 4, the product obtained in the previous step (1.57 g) was converted to (7α,14β,16β,17α)-17-[[[(1,1-dimethylethyl)dimethylsilyl]oxy]methyl]-3-methoxy-7-methylestra-1,3,5(10)-trien-16-ol (1.98 g).

v)—Tetrapropylammonium perruthenate (0.080 g) was added to a solution of the product obtained in the previous step (1.69 g) and 4-methylmorpholine N-oxide (1.33 g) in acetone (31 ml). After 1.5 h stirring at room temperature the reaction mixture was filtered over dicalite and silica The filtrate was concentrated under reduced pressure. Column chromatography of the crude product gave (7α,14β,17α)-17-[[[(1,1-dimethylethyl)dimethylsilyl]oxy]methyl]-3-methoxy-7-methylestra-1,3,5(10)-trien-16-one (1.02 g).

vi)—A solution of 1,1,1,3,3,3-hexamethyldisilazane (0.98 ml) in dry tetrahydrofuran (2.3 ml), cooled to 0° C., was treated with n-butyllithium (1.6 M solution in hexane, 2.87 ml). After 5 min. stirring, a solution of the product obtained in the previous step (1.02 g) in dry tetrahydrofuran (2.3 ml) was added and stirring was continued for 1 h. N-Phenyltrifluoromethanesulfonimide (2.5 g) was added and the reaction mixture was stirred for another 2 h. The reaction mixture was poured into a saturated aqueous solution of ammonium chloride and the product was extracted into ethyl acetate. The combined organic phases were washed with brine, dried over sodium sulfate and concentrated under reduced pressure. Column chromatography afforded (7α,14β,17α)-17-[[[(1,1-dimethylethyl)dimethylsilyl]oxy]methyl]-3-methoxy-7-methyl-16-[[(trifluoromethyl)sulfonyl]oxy]estra-1,3,5(10),15-tetraene (0.69 g).

vii)—A solution of the product obtained in the previous step (0.69 g) in dry dimethyl formamide (7.8 ml) was treated with palladium(II)acetate (37.9 mg), triphenylphosphine (89.7 mg), formic acid (0.322 ml), and diisopropylethylamine (3.10 ml) and the mixture was heated at 60° C. for 30 min. The reaction mixture was poured into water and the product was extracted into ethyl acetate. The combined organic phases were washed with brine, dried over sodium sulfate and concentrated under reduced pressure. Column chromatography afforded (7α,14β,7α)-17-[[[(1,1-dimethylethyl)dimethylsilyl]oxy]methyl]-3-methoxy-7-methylestra-1,3,5(10),15-tetraene (0.48 g).

viii)—Lithium granulate (0.80 g) was added in portions to a refluxing solution of the product obtained in the previous step (0.48 g) in dry tetrahydrofuran (40 ml) and liquid ammonia (90 ml) and the reaction mixture was stirred for 3 h. Dry tert-butanol (2 ml) was added dropwise land stirring was continued for 30 min. Ethanol was added and the ammonia was allowed to evaporate. Water was added and the product was extracted into ethyl acetate. The combined organic phases were washed with brine, dried over sodium sulfate and concentrated under reduced pressure, to give (7α,14β,17α)-17-[[[(1,1-dimethylethyl)dimethylsilyl]oxy]methyl]-3-methoxy-7-methylestra-2,5(10),15-triene (0.51 g). The product was used in the following step without further purification.

ix)—Following a procedure analogous to that described under iv of Example 1, the diene obtained in the previous step (0.51 g) was converted to (7α,14β,17α)-17-(hydroxymethyl)-7-methylestra-4,15-dien-3-one, $^1$H NMR δ 6.10 (dm, 1H, J=6.7 Hz), 5.83 (m, 1H), 5.71 (dm, 1H, J=6.7 Hz), 3.75 (m, 1H), 3.65 (m, 1H), 1.26 (s, 3H), 1.11 (m, 2H), 0.97 (t, 3H, J=7.1 Hz).

EXAMPLE 6

(7α,14β,17α)-17-(Hydroxymethyl)-7,14-dimethylestr-4-en-3-one i)—Following a procedure analogous to that described under iii of Example 5, (7α,17β)-3-methoxy-7-methylestra-1,3,5(10),14-tetraen-17-ol (Example 4, step i; 15.0 g) was converted to (7α,17β)-17-[[(1,1-dimethylethyl)dimethylsilyl]oxy]-3-methoxy-7-methylestra-1,3,5(10),14-tetraene (21.9 g). The product was used in the next step without further purification.

ii)—A solution of the product obtained in the previous step (19.33 g) in dry tetrahydrofuran (20 ml) was treated with borane-methylsulfide complex (27 ml) and the reaction mixture was stirred at room temperature for 2 h. Then it was diluted with tetrahydrofuran (350 ml) and cooled to 0° C. An aqueous solution of sodium hydroxide (2 M, 125 ml) was added carefully, followed by aqueous hydrogen peroxide (30%, 80 ml). The mixture was stirred at room temperature overnight. Then it was poured into brine and the product was extracted into ethyl acetate. The combined organic phases were washed with a saturated aqueous solution of sodium thiosulfate and brine, dried over sodium sulfate and concentrated under reduced pressure. Column chromatography afforded (7α,15β,17β)-17-[[(1,1-dimethylethyl)dimethylsilyl]oxy]-3-methoxy-7-methylestra-1,3,5(10)-trien-15-ol (7.64 g) and (7α,14β,15β,17β)-17-[[(1,1-dimethylethyl)dimethylsily]oxy]-3-methoxy-7-methylestra-1,3,5(10)-trien-15-ol (2.43 g).

iiia)—Following a procedure analogous to that described under v of Example 5, the 15α-hydroxy compound obtained in the previous step (7.42 g) was converted to (7α,17β)-17-[[(1,1-dimethylethyl)dimethylsilyl]oxy]-3-methoxy-7-methylestra-1,3,5(10)-trien-15-one (8.48 g).

iiib)—Following a procedure analogous to that described under v of Example 5, the 15β-hydroxy compound obtained in step ii (2.23 g) was converted to (7α,14β,17β)-17-[[(1,1-dimethylethyl)dimethylsilyl]oxy]-3-methoxy-7-methylestra-1,3,5(10)-trien-15-one (2.20 g).

iv)—A solution of the products of step iiia and iiib (10.68 g totally) in a mixture of dry tetrahydrofuran (68 ml) and dry tert-butanol (203 ml) was treated with potassium tert-butoxide (12.6 g) and the reaction mixture was stirred at room temperature for 1 h. Iodomethane (34 ml) was added and stirring was continued for 2 h. The reaction mixture was poured into a saturated aqueous solution of ammonium chloride and the product was extracted into ethyl acetate. The combined organic phases were washed with water and brine, dried over sodium sulfate and concentrated tinder reduced pressure, to give (7α,14β)-3-methoxy-7,14-dimethylestra-1,3,5(10),16-tetraen-15-one (7.67 g). The product was used in the following step without further purification.

v)—Aqueous hydrogen peroxide (30%, 300 ml) was added in 30 ml aliquots, at intervals of 30 min., while maintaining the temperature between 15° C. and 20° C., to a stirred solution of the product obtained in the previous step (3.77 g) in a mixture of tetrahydrofuran (600 ml) and tert-butanol (600 ml), containing aqueous potassium hydroxide (20%, 18 ml). The reaction mixture was stirred overnight (15<T<20° C.) and then poured into a mixture of water and brine (1:1). The product was extracted into ethyl acetate; the combined organic phases were washed with brine, a saturated aqueous solution of sodium thiosulfate, and brine, dried over sodium sulfate and concentrated under reduced pressure, to give (7α,14β,16β,17β)-16,17-epoxy-3-methoxy-7,14-dimethylestra-1,3,5(10)-trien-15-one (3.55 g). The product was used in the following step without further purification.

vi)—Lithium aluminium hydride (0.565 g) was added to a solution of the product obtained in the previous step (5.65 g) in dry tetrahydrofuran (113 ml), cooled to 0° C. The reaction mixture was heated under reflux for 1 h. After cooling, it was quenched with a saturated aqueous solution of sodium sulfate. The resulting mixture was filtered and the filtrate was concentrated under reduced pressure. Column chromatography afforded (7α,14β,15β,17β)-3-methoxy-7,14-dimethylestra-1,3,5(10)-triene-15,17-diol (2.27 g).

vii)—Benzoyl chloride (0.60 ml) was added to a solution of the product obtained in the previous step (1.70 g) in dry pyridine (20.6 ml), cooled to 0° C. The reaction mixture was stirred at 0° C. for 4 h; additional portions of benzoyl chloride (0.15 ml) were added after 2 and 3 h, respectively. Water was added and stirring was continued at room temperature for 1 h. The reaction mixture was poured into a saturated aqueous solution of sodium hydrogencarbonate and the product was extracted into ethyl acetate. The combined organic phases were washed with brine, dried over sodium sulfate and concentrated under reduced pressure. Column chromatography afforded (7α,14β,15β,17β)-3-methoxy-7,14-dimethylestra-1,3,5(10)-triene-15,17-diol 17-benzoate (1.53 g).

viii)—Pyridinium p-toluenesulfonate (0.30 g) was added to a solution of the product obtained in the previous step (1.31 g) in a mixture of dry dichloromethane (18 ml) and ethyl vinyl ether (6 ml). After 2 h stirring at room temperature, the reaction mixture was poured into a saturated aqueous solution of sodium hydrogencarbonate. The product was extracted into diethyl ether; the combined organic phases were washed with brine, dried over sodium sulfate and concentrated under reduced pressure, to give (7α,14β,15β,17β)-15-[(1-ethoxyethyl)oxy]-3-methoxy-7,14-dimethylestra-1,3,5(10)-trien-17-ol benzoate (1.64 g). The product was used in the following step without further purification.

ix)—A solution of the product obtained in the previous step (1.64 g) in dry tetrahydrofuran (70 ml) was added dropwise to a suspension of lithium aluminium hydride (0.50 g) in tetrahydrofuran (30 ml). After stirring of the mixture for 30 min., the reaction was quenched by addition of a saturated aqueous solution of sodium sulfate. The reaction mixture was filtered over dicalite and the filtrate was concentrated under reduced pressure, to give (7α,14β,15β,17β)-15-[(1-ethoxyethyl)oxy]-3-methoxy-7,14-dimethylestra-1,3,5(10)-trien-17-ol (1.50 g). The product was used in the following step without further purification.

x)—Following a procedure analogous to that described under v of Example 5, the product obtained in the previous step (1.50 g) was converted to (7α,14β,15β)-15-[(1-ethoxyethyl)oxy]-3-methoxy-7,14-dimethylestra-1,3,5(10)-trien-17-one (1.55 g).

xi)—Sodium hydride (60% suspension in mineral oil, 0.60 g) was added to a solution of the product obtained in the previous step (1.55 g) in a mixture of dry tetrahydrofuran (15 ml) and dry 2-propanol (30 ml). After 5 min. stirring at room temperature, the mixture was poured into a saturated aqueous solution of ammonium chloride. The product was extracted into diethyl ether; the combined organic phases were washed with brine, dried over sodium sulfate and concentrated under reduced pressure. Column chromatography afforded (7α,14β(3)-3-methoxy-7,14-dimethylestra-1,3,5(10),15-tetraen-17-one (1.01 g).

xii)—A solution of the product obtained in the previous step (0.90 g) and triethylsilane (1.8 ml) in dichloromethane (18 ml) was cooled to −40° C. Titanium(IV) chloride (1.0 ml) was added dropwise and the reaction mixture was stirred at −30° C. for 30 min. The reaction mixture was poured into a saturated aqueous solution of sodium hydrogencarbonate and the product was extracted into diethyl ether. The combined organic phases were washed with brine, dried over sodium sulfate and concentrated under reduced pressure, to give (7α,14β)-3-methoxy-7,14-dimethylestra-1,3,5(10)-trien-17-one (0.89 g). The product was used in the following step without further purification.

xiii)—Following a procedure analogous to that described under iii of Example 4, the product obtained in the previous step (0.68 g) was converted to (7α,14β)-3-methoxy-7,14-dimethyl-17-methyleneestra-1,3,5(10)-triene (0.50 g).

xiv)—Following a procedure analogous to that described under ii, the product obtained in the previous step (0.50 g) was converted to a mixture of (7α,14β,17α)-3-methoxy-7,14-dimethylestra-1,3,5(10)-triene-17-methanol and (7α,14β,17β)-3-methoxy-7,14-dimethylestra-1,3,5(10)-triene-17-methanol (0.35 g, ratio 1:1).

xv)—Following a procedure analogous to that described under v of Example 4, the product obtained in the previous step (0.35 g) was converted to a mixture of (7α,14β,17α)-3-methoxy-7,14-dimethylestra-2,5(10)-diene-17-methanol and (7α,14β,17β)-3-methoxy-7,14-dimethylestra-2,5(10)-diene-17-methanol (0.39 g, ratio 1:1).

xvi)—Following a procedure analogous to that described under iv of Example 1, the product obtained in the previous step (0.39 g) was converted to a mixture of (7α,14β,17α)-17-(hydroxymethyl)-7,14-dimethylestr-4-en-3-one and (7α,14β,17β)-17-(hydroxymethyl)-7,14-dimethylestr-4-en-3-one (0.16 g, ratio 1:1), $^1$H NMR δ 5.80 (m, 1H), 3.83 (dd, 0.5H, J=10.2 and 6.0 Hz), 3.74 (dd, 0.5H, J=10.2 and 5.6 Hz), 3.52 (m, 1H), 1.01 (s, 1.5H), 0.97 (s, 1.5H), 0.93 (s, 1.5H), 0.91 (s, 1.5H), 0.80 (d, 1.5H, J=7.0 Hz), 0.78 (d, 1.5H, J=7,2 Hz).

EXAMPLE 7

(7α,14β,15β,17α)-17-(Hydroxymethyl)-7,15-dimethylestr-4-en-3-one i)—p-Toluenesulfonic acid (0.248 g) was added to a solution of (7α,14β)-3-methoxy-7-methylestra-1,3,5(10)-trien-17-one (Example 4, step ii; 5.0 g) in a mixture of ethylene glycol (8.0 ml) and triethyl orthoformate (14.5 ml). The reaction mixture was stirred at room temperature for 2.5 h. Water was added and stirring was continued for 1 h. The product was extracted into ethyl acetate; the combined organic phases were washed with a saturated aqueous solution of sodium hydrogencarbonate and brine, dried over sodium sulfate and concentrated under reduced pressure, to give (7α,14β)-3-methoxy-7-methylestra-1,3,5(10)-trien-17-one cyclic 1,2-ethanediyl acetal (6.14 g). The product was used in the following step without further purification.

ii)—Phenyltrimethylammonium tribromnide (4.75 g) was added to a solution of the product obtained in the previous step (5.41 g) in dry tetrahydrofuran (32 ml). After 1.5 h stirring the mixture was poured into a saturated aqueous solution of sodium thiosulfate. The product was extracted into ethyl acetate; the combined organic phases were washed with water and brine, dried over sodium sulfate and concentrated under reduced pressure, to give (7α,14β,16β)-16-bromo-3-methoxy-7-methylestra-1,3,5(10)-trien-17-one cyclic 1,2-ethanediyl acetal (8.17 g). The product was used in the following step without further purification.

iii)—A solution of the product obtained in the previous step (8.17 g) in dry dimethyl sulfoxide (32 ml) was treated with potassium tert-butoxide (7.10 g) and the reaction mixture was stirred at room temperature for 1 h. Additional potassium tert-butoxide (3.50 g) was added and the reaction mixture was stirred for another 2 h. The mixture was poured into a saturated aqueous solution of ammonium chloride and the product was extracted into ethyl acetate. The combined organic phases were washed with water and brine, dried over sodium sulfate and concentrated under reduced pressure, to give (7α,14β)-3-methoxy-7-methylestra-1,3,5(10),15- tetraen-17-one cyclic 1,2-ethanediyl acetal (5.48 g). The product was used in the following step without further purification.

iv)—A solution of the product obtained in the previous step (5.84 g) in a mixture of acetone (98 ml) and water (8.2 ml) was treated with p-toluenesulfonic acid (0.283 g) and the reaction mixture was stirred at room temperature for 2.5 h. Then it was poured into a saturated aqueous solution of sodium hydrogencarbonate and the product was extracted into ethyl acetate. The combined organic phases were washed with brine, dried over sodium sulfate and concentrated under reduced pressure. Column chromatography afforded (7α,14β)-3-methoxy-7-methylestra-1,3,5(10),15-tetraen-17-one (2.90 g).

v)—A solution of the product obtained in the previous step (2.17 g) in dry tetrahydrofuran (107 ml), containing copper(II)acetate (0.73 g), was cooled to –20° C. Methylmagnesium chloride (3 M solution in tetrahydrofuran, 18.0 ml) was added dropwise and the reaction mixture was stirred for 1 h. Then it was poured into a saturated aqueous solution of ammonium chloride and the product was extracted into ethyl acetate. The combined organic phases were washed with a saturated aqueous solution of ammonium chloride and brine, dried over sodium sulfate and concentrated under reduced pressure, to give (7α,14β,15β)-3-methoxy-7,15-dimethylestra-1,3,5(10)trien-17-one (2.38 g). The product was used in the following step without further purification.

vi)—Following a procedure analogous to that described under iii of Example 4, the product obtained in the previous step (1.96 g) was converted to (7α,14β,15β)-3-methoxy-7,15-dimethyl-17-methyleneestra-1,3,5(10)-triene (1.30 g).

vii)—Following a procedure analogous to that described under iv of Example 4, the product obtained in the previous step (1.30 g) was converted to (7α,14β,15β,17α)-3-methoxy-7,15-dimethylestra-1,3,5(10)-triene-17-methanol (0.93 g).

viii)—Following a procedure analogous to that described under v of Example 4, the product obtained in the previous step (0.93 g) was converted to (7α,14β,15β,17α)-3-methoxy-7,15-dimethylestra-2,5(10)-diene-17-methanol (0.93 g).

ix)—Following a procedure analogous to that described under iv of Example 1, the product obtained in the previous step (0.93 g) was converted to (7α,14β,15β,17α)-17-(hydroxymethyl)-7,15-dimethylestr-4-en-3-one (0.27 g), $[\alpha]_D^{20}$=+93.2 (c=0.56, dioxane).

EXAMPLE 8

(7α,14β,16α,17α)-17-(Hydroxymethyl)-7,16-dimethylestr-4-en-3-one i)—A solution of lithium bis(trimethylsilyl)amide (55.5 mmol) in tetrahydrofuran (96 ml) was cooled to 40° C. A solution of (7α,14β)-3-methoxy-7-methylestra-1,3,5(10)-trien-17-one (Example 4, step ii; 15.0 g) in dry tetrahydrofuran (66 ml) was added dropwise and the reaction mixture was stirred for 45 min. Then, at –30° C., iodomethane (6.3 ml) was added and stirring was continued for 1 h (–30<T –20° C.). The mixture was poured into a saturated aqueous solution of ammonium chloride and the product was extracted into ethyl acetate. The combined organic phases were washed with water and brine, dried over sodium sulfate and concentrated under reduced pressure, to give (7α,14β,16β)-3-methoxy-7,16-dimethylestra-1,3,5(10)-trien-17-one (17.33 g). The product was used in the following step without further purification.

ii)—A solution of lithium bis(trimethylsilyl)amide (29 mmol) in tetrahydrofuran (45 ml) was cooled to 40° C. A solution of the product obtained in the previous step (6.0 g) in dry tetrahydrofuran (24 ml) was added dropwise and the reaction mixture was stirred for 1 h. Then it was poured into a saturated aqueous solution of ammonium chloride and the product was extracted into ethyl acetate. The combined organic phases were washed with water and brine, dried over sodium sulfate and concentrated under reduced pressure, to give (7α,14β,16α)-3-methoxy-7,16-dimethylestra-1,3,5(10)-trien-17-one (6.82 g). The product was used in the next step without further purification.

iii)—Following a procedure analogous to that described under iii of Example 4, the product obtained in the previous step (5.14 g) was converted to a mixture of (7α,14β16α)-3-methoxy-7,16-dimethyl-17-methyleneestra-1,3,5(10)-triene and (7α,14β,16β)-3-methoxy-7,16-dimethyl-17-methyleneestra-1,3,5(10)-triene (3.78 g, ratio 1:1).

iv)—Following a procedure analogous to that described under iv of Example 4, the product obtained in the previous step (4.56 g) was converted to (7α,14β,16α,17α)-3-methoxy-7,16-dimethylestra-1,3,5(10)-triene-17-methanol (2.40 g) and (7α,14β,16β,17β)-3-methoxy-7,16-dimethylestra-1,3,5(10)-triene-17-methanol (0.70 g).

v)—Following a procedure analogous to that described under v of Example 4, (7α,14β,16α,17α)-3-methoxy-7,16-dimethylestra-1,3,5(10)-triene-17-methanol (2.31 g converted to (7α,14β,16α,17α)-3-methoxy-7,16-dimethylestra-2,5(10)-diene-17-methanol (2.41 g).

vi)—Following a procedure analogous to that described under iv of Example 1, the product obtained in the previous step (2.41 g) was converted to (7α,14β,16α,17α)-17-(hydroxymethyl)-7,16-dimethylestr-4-ene-3-one (0.92 g), $[\alpha]_D^{20}$=+64.1° (c=0.535, dioxane).

EXAMPLE 9

(7α,14β,16β,17α)-17-(Hydroxymethyl)-7,16-dimethylestr-4-en-3-one i)—m-Chloroperbenzoic acid (70–75%, 1.7 g) was added to a solution of a mixture of (7α,14β,16α)-3-methoxy-7,16-dimethyl-17-methyleneestra-1,3,5(10)-triene and (7α,14β,16β)-3-methoxy-7,16-dimethyl-17-methyleneestra-1,3,5(10)-triene (Example 8, step iii; 5.58 g, ratio 1:1) in dichloromethane (100 ml). The reaction mixture was stirred at room temperature for 6 h; additional portions of m-chloroperbenzoic acid (1.7 g and 0.64 g) were added after 1.5 h and 2.5 h, respectively. The reaction was poured into a saturated aqueous solution of sodium sulfite and the mixture was stirred at room temperature for 1 h. The product was extracted into dichloromethane; the combined organic phases were washed with an aqueous solution of sodium hydroxide (10%) and brine, dried over sodium sulfate and concentrated under reduced pressure. Column chromatography afforded a mixture of (7α,14β,16β,17α)-3-methoxy-7,16-dimethylspiroestra-1,3,5(10)-triene[17,2']oxirane and (7α,14β,16β,17α)-3-methoxy-7,16-dimethylspiroestra-1,3,5(10)-triene[17,2']oxirane (2.31 g, ratio 1:1).

ii)—A solution of the product obtained in the previous step (1.45 g) in 1,4-dioxane (44 ml) was treated with an aqueous solution of perchloric acid (70%, 0.29 ml). The reaction mixture was stirred at room temperature for 45 min. and then poured into a saturated aqueous solution of sodium hydrogencarbonate. The product was extracted into ethyl acetate; the combined organic phases were washed with brine, dried over sodium sulfate and concentrated under reduced pressure, to give (7α,14β,16β,17α)-3-methoxy-7,16-dimethylestra-1,3,5(10)-triene-17-carboxaldehyde (1.42 g). The product was used in the following step without further purification.

iii)—Following a procedure analogous to that described under ix of Example 6, the product obtained in the previous step (1.42 g) was converted to (7α,14β,16β,17α)-3-methoxy-7,16-dimethylestra-1,3,5(10)-triene-17-methanol (0.52 g).

iv)—Following a procedure analogous to that described under v of Example 4, the product obtained in the previous step (0.80 g) was converted to (7α,14β,16β,17α)-3-methoxy-7,16-dimethylestra-2,5(10)-diene-17-methanol (0.64 g).

v)—Following a procedure analogous to that described under iv of Example 1, the product obtained in the previous step (0.64 g) was converted to (7α,14β,16β,17α)-17-(hydroxymethyl)-7,16-dimethylestr-4-en-3-one (0.22 g), $[\alpha]_D^{20}$=+101.0 (c 0.49, dioxane).

EXAMPLE 10

(7α,14β,15β,16β,17α)-17-(Hydroxymethyl)-7-methyl-15,16-methyleneestr-4-en-3-one i)—Sodium hydride (60% suspension in mineral oil, 1.15 g) was added to a suspension of trimethylsulfoxonium iodide (5.57 g) in dry dimethyl sulfoxide (115 ml) and the mixture was stirred at room temperature for 20 min. (7α,14β)-3-Methoxy-7-methylestra-1,3,5(10),15-tetraen-17-one (Example 7, step iv; 1.92 g) was added and stirring was continued for 1.5 h. The reaction mixture was poured into ice-water and the product was extracted into ethyl acetate. The combined organic phases were washed with water and brine, dried over sodium sulfate and concentrated under reduced pressure, to give (7α,14β,15β,16β)-3-methoxy-7-methyl-15,16-methyleneestra-1,3,5(10)-trien-17-one (2.65 g). The product was used in the following step without further purification.

ii)—Potassium tert-butoxide (2.56 g) was added in portions to a solution of the product obtained in the previous step (2.25 g) in dry dimethylformamide (58 ml), containing trimethylsulfonium iodide (3.2 g). The reaction mixture was stirred at room temperature for 1.5 h and then poured into an aqueous solution of ammonium chloride. The product was extracted into ethyl acetate; the combined organic phases were washed with water and brine, dried over sodium sulfate and concentrated under reduced pressure, to obtain (7α,14β,15β,16β,17α)-3-methoxy-7-methyl-15,16-methylenespiroestra-1,3,5(10)-triene[17,2']oxirane (2.31 g). The product was used in the following step without further purification.

iii)—Following a procedure analogous to that described under ii of Example 9, the product obtained in the previous step (2.31 g) was converted to (7α,14β,15β,16β,17α)-3-methoxy-7-methyl-15,16-methyleneestra-1,3,5(10)-triene-17-carboxaldehyde (2.27 g).

iv)—Following a procedure analogous to that described under ix of Example 6, the product obtained in the previous step (0.70 g) was converted to (7α,14β,15β,16β,17α)-3-methoxy-7-methyl-15,16-methyleneestra-1,3,5(10)-triene-17-methanol (0.38 g).

v)—Following a procedure analogous to that described under v of Example 4, the product obtained in the previous step (0.38 g) was converted to (7α,14β,15β,16β,17α)-3-methoxy-7-methyl-15,16-methyleneestra-2,5(10)-diene-17-methanol (0.36 g). vi)—Following a procedure analogous to that described under iv of Example 1, the product obtained in the previous step (0.36 g) was converted to (7α,14β,15β,16β,17α-17-(hydroxymethyl)-7-methyl-15,16-methyleneestr-4-en-3-one (0.21 g), $[\alpha]_D^{20}$=+67.6 (c=0.58, dioxane).

EXAMPLE 11

(7α,14β,17α)-17-(Hydroxymethyl)-7,17-dimethylestr-4-en-3-one i)—Following a procedure analogous to that described under step ii of Example 4, using the double amount of Jones reagent, (7α,14β,17α)-3-methoxy-7-methylestra-1,3,5(10)-triene-17-methanol (Example 4, step iv; 2.0 g) was converted to (7α,14β,17α)-3-methoxy-7-methylestra-1,3,5(10)-triene-17-carboxylic acid (2.09 g).

ii)—A solution of the product obtained in the previous step (2.09 g) and dry pyridine (0.77 ml) in dry toluene (50 ml), cooled to 5–10° C., was treated with a solution of oxalyl chloride (0.77 ml) in dry toluene (1 ml). The reaction mixture was stirred at room temperature for 2 h. After cooling to 0–5° C., dry methanol (2.6 ml) was added dropwise and stirring was continued at 10–15° C. for 1.5 h. The mixture was poured into ice-water and the product was extracted into ethyl acetate. The combined organic phases were washed with water and brine, dried over sodium sulfate and concentrated under reduced pressure, to give methyl (7α,14β,17α)-3-methoxy-7-methylestra-1,3,5(10)-triene-17-carboxylate (2.30 g). The product was used in the following step without further purification.

iii)—A solution of diisopropylamine (2.38 ml) in dry tetrahydrofuran (5 ml), cooled to −70° C., was treated with n-butyllithium (1.6 M solution in hexane, 8.86 ml). The mixture was warmed-up to 0° C. and then cooled to −70° C. A solution of the product obtained in the previous step (1.94 g) in dry tetrahydrofuran (4 ml) was added and the temperature was allowed to raise to 0° C. After cooling to −70° C., a solution of iodomethane (1.06 ml) in dry tetrahydrofuran (2 ml) was added dropwise. The cooling bath was removed, the reaction mixture was stirred for 2 h and then poured into a saturated aqueous solution of ammonium chloride. The product was extracted into ethyl acetate; the combined organic phases were washed with water and brine, dried over sodium sulfate and concentrated under reduced pressure, to give methyl (7α,14β,17α)-3-methoxy-7,17-dimethylestra-1,3,5(10)-triene-17-carboxylate (2.10 g). The product was used in the following step without further purification.

iv)—Following a procedure analogous to that described under step ix of Example 6, the product obtained in the previous step (2.1 g) was converted to (7α,14β,17α)-3-methoxy-7,17-dimethylestra-1,3,5(10)-triene-17-methanol (1.81 g).

v)—Lithium granulate (1.16 g) was added in portions to a refluxing solution of the alcohol obtained in the previous step (1.81 g) in dry tetrahydrofuran (40 ml) and liquid ammonia (120 ml). After 30 min. stirring, dry ethanol (10 ml) was added dropwise. Stirring was continued for 30 min.; solid ammonium chloride (3.5 g) was added and the ammonia was allowed to evaporate. Water was added and the product was extracted into ethyl acetate. The combined organic phases were washed with brine, dried over sodium sulfate and concentrated under reduced pressure, to give (7α,14β,17α)-3-methoxy-7,17-dimethylestra-2,5(10)-diene-17-methanol (1.73 g). The product was used in the following step without further purification.

vi)—Following a procedure analogous to that described under step iv of Example 1, the product obtained in the previous step (1.73 g) was converted to (7α,14β,17α)-17-(hydroxymethyl)-7,17-dimethylestr-4-en-3-one (0.82 g), m.p. 190–192° C.

EXAMPLE 12

(7α,14β,17α)-17-Fluoro-17-(hydroxymethyl)-7-methylestr-4-en-3-one i)—Following a procedure analogous to that described under i of Example 9, (7α,14β)-3-methoxy-7-methyl-17-methyleneestra-1,3,5(10)-triene (Example 4, step iii; 2.96 g) was converted to (7α,14β,17β)-3-methoxy-7-methylspiroestra-1,3,5(10)-triene[17,2']oxirane (2.94 g).

ii)—A solution of the epoxide obtained in the previous step (0.31 g) in dry dichloromethane (10 ml) was cooled to 0° C. Hydrogen fluoride-pyridine (70% HF, 0.1 ml) was added and the reaction mixture was stirred for 3 h. Another portion of hydrogen fluoride-pyridine (0.1 ml) was added and the reaction mixture was stirred for another 3 h. The mixture was poured into a saturated aqueous solution of sodium hydrogencarbonate. The product was extracted into dichloromethane; the combined organic phases were washed with a saturated aqueous solution of sodium hydrogencarbonate and brine, dried over sodium sulfate, and concentrated under reduced pressure. Column chromatography afforded (7α,14β,17α)-17-fluoro-3-methoxy-7-methylestra-1,3,5(10)-triene-17-methanol, contaminated with (7α,14β)-3-methoxy-7-methylestra-1,3,5(10),16-tetraene-17-methanol (0.12 g).

iii)—A solution of the mixture obtained in the previous step (0.12 g), dry pyridine (0.50 ml) and acetic anhydride (0.30 ml) in dry tetrahydrofuran (5 ml) was stirred at room temperature for 72 h. The reaction mixture was poured into ice-water, and after 1 h stirring, the product was extracted into ethyl acetate. The combined organic phases were washed with a saturated aqueous solution of sodium hydrogencarbonate and brine, dried over sodium sulfate, and concentrated under reduced pressure. Column chromatography afforded (7α,14β,17α)-17-[(acetyloxy)methyl]-17-fluoro-3-methoxy-7-methylestra-1,3,5(10)-triene (0.090 g).

iv)—Following a procedure analogous to that described under v of Example 11, the product obtained in the previous step (0.080 g) was converted to (7α,14β,17α)-17-fluoro-3-methoxy-7-methylestra-2,5(10)-diene-17-methanol (0.080 g).

v)—Following a procedure analogous to that described under iv of Example 1, the product obtained in the previous step (0.080 g) was converted to (7α,14β,17α)-17-fluoro-17-(hydroxymethyl)-7-methylestr-4-en-3-one (0.026 g). M.p. 145–146° C.

EXAMPLE 13

(7α,14β,17β)-17-Hydroxy-17-(hydroxymethyl)-7-methylestr-4-en-3-one i)—A solution of (7α,14β,17β)-3-methoxy-7-methylspiroestra-1,3,5(10)-triene[17,2']oxirane (Example 12, step i; 0.91 g) in tert-butanol (70 ml), containing potassium hydroxide (4.5 g), was refluxed overnight. The reaction mixture was poured into water and neutralized with aqueous hydrochloric acid (2 M). The product was extracted into ethyl acetate; the combined organic phases were washed with brine, dried over sodium sulfate and concentrated under reduced pressure. Column chromatography afforded (7α,14β,17β)-17-hydroxy-3-methoxy-7-methylestra-1,3,5(10)-triene-17-methanol (0.21 g).

ii)—Following a procedure analogous to that described under iii of Example 1, the product obtained in the previous step (0.21 g) was converted to (7α,14β,17β)-17-hydroxy-3-methoxy-7-methylestra-2,5(10)-diene-17-methanol (0.21 g).

iii)—Following a procedure analogous to that described under iv of Example 1, using methanol as solvent, the product obtained in the previous step (0.13 g) was converted to (7α,14β,17β)-17-hydroxy-17-(hydroxymethyl)-7-methylestr-4-en-3-one (0.093 g), m.p. 163–167° C.

EXAMPLE 14

(7α,14β,17α)-7-Ethyl-17-(hydroxymethyl)estr-4-en-3-one i)—Vinylmagnesium chloride in tetrahydrofuran (2 M, 159.2 ml) was added dropwise to a mixture of (17β)-17-(acetyloxy)estra-4,6-diene-3-one [Syntex, DE 1143199 (1963); 50.0 g], copper(I) bromide-dimethyl sulfide complex (3.18 g), lithium bromide (1.38 g), and lithium thiophenoxide (16 ml of a 1 M solution in tetrahydrofuran), in dry tetrahydrofuran (167 ml), cooled to −15° C. After 30 min. stirring a saturated aqueous solution of ammonium chloride was added and the product extracted into ethyl acetate. The combined organic phases were concentrated under reduced pressure whereafter the residue was dissolved in acetone (1000 ml) and treated with hydrochloric acid (4 M, 100 ml). After 30 min. stirring at room temperature, the mixture was poured into a saturated aqueous solution of sodium hydrogencarbonate. Part of the acetone was removed under reduced pressure and the product was extracted into ethyl acetate. The combined organic phases were washed with brine, dried over sodium sulfate and concentrated under reduced pressure, to give (7α,17β)-17-(acetyloxy)-7-ethenylestr-4-en-3-one (59.4 g). The product was used in the following step without further purification.

ii)—Powdered potassium hydroxide (26.7 g) was added to a solution of the product obtained in the previous step (59.4 g) in a mixture of tetrahydrofuran (833 ml), methanol (738 ml), and water (238 ml). The reaction mixture was stirred at room temperature for 45 min. and then neutralized with concentrated hydrochloric acid (20 ml). The tetrahydrofuran and the methanol were removed under reduced pressure and the product was extracted into ethyl acetate. The combined organic phases were washed with water and brine, dried over sodium sulfate and concentrated under reduced pressure. Column chromatography afforded (7α,17β)-7-ethenyl-17-hydroxyestren-3-one (34.46 g).

iii)—A mixture of the product obtained in the previous step (66.24 g), trimethyl orthoformate (80 ml), copper(II) bromide (65.18 g), and methanol (1788 ml) was heated under reflux for 50 min. After cooling, the reaction mixture was filtered. The filtrate was concentrated under reduced pressure and the residu dissolved in ethyl acetate. The resulting solution was washed with a saturated aqueous solution of sodium hydrogencarbonate and brine, dried over sodium sulfate and concentrated under reduced pressure. Column chromatography afforded (7α,17β)-7-ethenyl-3-methoxyestra-1,3,5(10)-trien-17-ol (42.90 g).

iv)—Following a procedure analogous to that described under v of Example 5, the product obtained in the previous step (41.1 g) was converted to (7α)-7-ethenyl-3-methoxyestra-1,3,5(10)-trien-17-one(38.1 g).

v)—Following a procedure analogous to that described under i of Example 7, the product obtained in the previous step (36.05 g) was converted to (7α)-7-ethenyl-3-methoxyestra-1,3,5(10)-trien-17-one cyclic 1,2-ethanediyl acetal (41.37 g).

vi)—Following a procedure analogous to that described under ii of Example 7, the product obtained in the previous step (20.0 g) was converted to (7α,16α)-16-bromo-7-ethenyl-3-methoxyestra-1,3,5(10)-trien-17-one cyclic 1,2-ethanediyl acetal (28.05 g).

vii)—Following a procedure analogous to that described under iii of Example 7, the product obtained in the previous step (28.05 g) was converted to (7α)-7-ethenyl-3-methoxyestra-1,3,5(10),15-tetraen-17-one cyclic 1,2-ethanediyl acetal (13.93 g).

viii)—Following a procedure analogous to that described under iv of Example 7, the product described in the previous step (31.47 g) was converted to (7α)-7-ethenyl-3-methoxyestra-1,3,5(10),15-tetraen-17-one (23.92 g).

ix)—A solution of the ketone obtained in the previous step (23.92 g) and p-toluenesulfonic acid (13.5 g) in toluene (970 ml) was heated under reflux for 15 min. After cooling, the reaction mixture was poured into a saturated aqueous solution of sodium hydrogencarbonate. The product was extracted into ethyl acetate; the combined organic phases were washed and brine, dried over sodium sulfate, and-concentrated under reduced pressure. Column chromatography afforded (7α)-7-ethenyl-3-methoxyestra-1,3,5(10),14-tetraen-17-one (14.9 g) and (7α,14β)-7-ethenyl-3-methoxyestra-1,3,5(10),15-tetraen-17-one (7.32 g).

x)—Sodium borohydride (8.54 g) was added to a solution of (7α)-7-ethenyl-3-methoxyestra-1,3,5(10),14-tetraen-17-one (8.72 g) in a mixture of tetrahydrofuran (161 ml), ethanol (161 ml), and water (26.4 ml). The reaction mixture was stirred at room temperature for 50 min. and then poured into water. The product was extracted into ethyl acetate; the combined organic phases were washed with water, a saturated aqueous solution of sodium hydrogencarbonate and brine, dried over sodium sulfate and concentrated under reduced pressure. Column chromatography afforded (7α,17β)-7-ethenyl-3-methoxyestra-1,3,5(10),14-tetraen-17-ol (8.45 g).

xi)—Following a procedure analogous to that described under i of Example 4, using Pd/C 10%, the product obtained in the previous step (4.0 g) was converted to (7α,14β,17β)-7-ethyl-3-methoxyestra-1,3,5(10)-trien-17-ol (3.57 g).

xii)—Following a procedure analogous to that described under v of Example 5, the product obtained in the previous step (3.57 g) was converted to (7α,14β)-7-ethyl-3-methoxyestra-1,3,5(10)-trien-17-one (2.65 g).

xiii)—Following a procedure analogous to that described under iii of Example 4, the product obtained in the previous step (1.90 g) was converted to (7α,14β)-7-ethyl-3-methoxy-17-methyleneestra-1,3,5(10)-triene (2.39 g).

xiv)—Following a procedure analogous to that described under iv of Example 4, the product obtained in the previous step (2.39 g) was converted to (7α,14β,17α)-7-ethyl-3-methoxyestra-1,3,5(10)-triene-17-methanol (2.67 g).

xv)—Following a procedure analogous to that described under v of Example 4, the product obtained in the previous step (2.67 g) was converted to (7α,14β,17α)-7-ethyl-3-methoxyestra-2,5(10)-diene-17-methanol (2.15 g).

xvi)—Following a procedure analogous to that described under iv of Example 1, the product obtained in the previous step (2.15 g) was converted to (7α,14β,7α)-7-ethyl-17-hydroxymethyl)estr-4-en-3-one (0.60 g), $[\alpha]_D^{20}$=+68 ° (c=0.50, dioxane).

EXAMPLE 15

(7α,14β,17α)-7-Ethenyl-17-(hydroxymethyl)estr-4-en-3-one i)—Following a procedure analogous to that described under xii of Example 6, (7α,14β)-7-ethenyl-3-methoxyestra-1,3,5(10),15-tetraen-17-one (Example 14, step ix; 3.18 g) was converted to (7α,14β,17α)-7-ethenyl-3-methoxyestra-1,3,5(10)-trien-17-ol (2.02 g).

ii)—Following a procedure analogous to that described under v of Example 5, the product obtained in the previous step (2.79 g) was converted to (7α,14β)-7-ethenyl-3-methoxyestra-1,3,5(10)-trien-17-one (2.44 g).

iii)—A solution of potassium tert-butoxide (7.57 g) in tert-butanol (68 ml) was added to a solution of the product obtained in the previous step (2.10 g) in dimethoxyethane (17 ml). A solution of tosylmethyl isocyanide (TosMIC, 2.64 g) in dry dimethoxyethane (34 ml) was added in 1.5 h and the reaction mixture was stirred for 2 h. Then it was poured into a saturated aqueous solution of ammonium chloride. The product was extracted into ethyl acetate; the combined organic phases were washed with water and brine, dried over sodium sulfate and concentrated under reduced pressure. Column chromatography afforded (7α,14β,17α)-7-ethenyl-3-methoxyestra-1,3,5(10)-triene-17-carbonitrile (1.91 g).

iv)—Diisobutylaluminum hydride (20% solution in toluene, 27.4 ml) was added to a solution of the product obtained in the previous step (1.81 g) in dry toluene (28 ml) while maintaining the temperature below 20° C. The reaction mixture was stirred for 50 min. and then quenched with aqueous acetic acid (20%). The resulting mixture was filtered and the filtrate was poured into a saturated aqueous solution of sodium hydrogencarbonate. The product was extracted into ethyl acetate; the combined organic phases were washed with brine, dried over sodium sulfate and concentrated under reduced pressure, to give (7α,14β,17α)-7-ethenyl-3-methoxyestra-1,3,5(10)-triene-17-carboxaldehyde (1.87 g). The product was used in the following step without further purification.

v)—Following a procedure analogous to that described under ix of Example 6, the product obtained in the previous step (1.87 g) was converted to (7α,14β,17α)-7-ethenyl-3-methoxyestra-1,3,5(10)triene-17-methanol (0.72 g).

vi)—Following a procedure analogous to that described under v of Example 4, the product obtained in the previous step (0.72 g) was converted to (7α,14β17α)-7-ethenyl-3-methoxyestra-2,5(10)-diene-17-methanol (0.71 g).

vii)—Following a procedure analogous to that described under iv of Example 1, the product obtained in the previous step (0.71 g) was converted to (7α,14β,17α)-7-ethenyl-17-(hydroxymethyl)estr-4-en-3-one (0.095 g), $[\alpha]_D^{20}$=−5.3 (c=0.75, dioxane).

3) 7,20-SUBSTITUTED COMPOUNDS

EXAMPLE 16

(7α,14β,17α,20S)-20-Hydroxy-7-methyl-19-norpregn-4-en-3-one (a) and (7α,14β,17α,20R)-20-Hydroxy-7-methyl-19-norpregn-4-en-3-one (b)

i)—Pyridinium chlorochromate (10.1 g) was added to a solution of (7α,14β,17α)-3-methoxy-7-methylestra-1,3,5 (10)-triene-17-methanol (Example 4, step iv; 5.90 g) in dichloromethane (295 ml) containing sodium acetate (8.85 g) and silica (17.7 g). After 3 h stirring at room temperature the reaction mixture was filtered over dicalite and the filtrate was concentrated under reduced pressure. Column chromatography afforded (7α,14β,17α)-3-methoxy-7-methylestra-1,3,5(10)-triene-17-carboxaldehyde (4.16 g).

ii)—Methylmagnesium chloride (3 M solution in tetrahydrofuran, 1.65 ml) was added dropwise to a solution of the aldehyde obtained in the previous step (1.40 g) in dry tetrahydrofuran (42 ml), cooled to 0° C. After 30 min. stirring, the reaction mixture was poured into a saturated aqueous solution of ammonium chloride. The product was extracted into ethyl acetate; the combined organic phases were washed with brine, dried over sodium sulfate and concentrated under reduced pressure. Column chromatography afforded (7α,14β,17α,20S)-3-methoxy-7-methyl-19-norpregna-1,3,5(10)-trien-20-ol (0.53 g) and (7α,14β,17α,20R)-3-methoxy-7-methyl-19-norpregna-1,3,5(10)-trien-20-ol (0.40 g).

iiia)—Following a procedure analogous to that described under v of Example 11, (7α,14β,17α,20S)-3-methoxy-7-methyl-19-norpregna-1,3,5(10)-trien-20-ol (0.53 g) was converted to (7α,14β,17α,20S)-3-methoxy-7-methyl-19-norpregna-2,5(10)-dien-20-ol (0.50 g).

iiib)—Following a procedure analogous to that described above, (7α,14β,17α,20R)-3-methoxy-7-methyl-19-norpregna-1,3,5(10)-trien-20-ol (0.40 g) was converted to (7α,14β,17α,20R)-3-methoxy-7-methyl-19-norpregna-2,5(10)-dien-20-ol (0.39 g).

iva)—Following a procedure analogous to that described under iv of Example 1, (7α,14β,17α,20S)-3-methoxy-7-methyl-19-norpregna-2,5(10)-dien-20-ol (0.50 g) was converted to (7α,14β,17α,20S)-20-hydroxy-7-methyl-19-norpregn-4-en-3-one (0.22 g), m.p. 157–160° C.

ivb)—Following a procedure analogous to that described under iv of Example 1, (7α,14β,17α,20R)-3-methoxy-7-methyl-19-norpregna-2,5(10)-dien-20-ol (0.39 g) was converted to (7α,14β,17α,20R)-20-hydroxy-7-methyl-19-norpregn-4-en-3-one (0.22 g), $[α]_D^{20}$=+75° (c=0.5, dioxane).

EXAMPLE 17

[7α,14β,17α(S)]-17-(1-Hydroxypropyl)-7-methylestr-4-en-3-one (a) and [7α,14β,17α(R)]-17-(1-Hydroxypropyl)-7-methylestr-4-en-3-one (b)

i)—Boron trifluoride diethyl etherate (0.60 ml) was added to a mixture of (7α,14β,17α)-17-(hydroxymethyl)-7-methylestr-4-en-3-one (Example 4; 15.5 g), 1,2-ethanedithiol (17 ml), and dry methanol (150 ml). After 2 h stirring at room temperature, a saturated aqueous solution of sodium hydrogencarbonate (50 ml) was added and the methanol was removed under reduced pressure. The product was extracted into ethyl acetate; the combined organic phases were washed with aqueous sodium hydroxide (10%), water and brine, dried over sodium sulfate and concentrated under reduced pressure. Column chromatography gave (7α,14β,17α)-17-(hydroxymethyl)-7-methylestr-4-en-3-one cyclic 1,2-ethanediyl dithioacetal (12.0 g).

ii)—A solution of the product obtained in the previous step (6.0 g) in dry dichloromethane (60 ml), containing dry pyridine (1 ml) was treated with pyridinium dichromate (6.0 g) and the reaction mixture was stirred at room temperature for 1 h. Additional pyridinium dichromate (6.0 g) was added and stirring was continued overnight. Silica (10 g) was added and after 10 min. stirring the mixture was filtered over silica. The residue was washed with ethyl acetate. The filtrate was washed with water and brine, dried over sodium sulfate and concentrated under reduced pressure. Trituration of the residue and column chromatography of the mother liquor gave (7α,14β,17α)-17-formyl-7-methylestr-4-en-3-one cyclic 3-(1,2-ethanediyl dithioacetal) (4.2 g).

iii)—Following a procedure analogous to that described under ii of Example 16, the product obtained in the previous step (1.0 g) was reacted with ethylmagnesium bromide, to give, after chromatography, [7α,14β,17α(S)]-17-(1-hydroxypropyl)-7-methylestr-4-en-3-one cyclic 1,2-ethanediyl dithioacetal (0.31 g) and [7α,14β,17α(R)]-17-(1-hydroxypropyl)-7-methylestr4-en-3-one cyclic 1,2-ethanediyl dithioacetal (0.075 g).

iva)—A solution of periodic acid (0.028 g) in a mixture of methanol and water (1:1, 2.24 ml) was added to a solution of [7α,14β,17α(S)]-17-(1-hydroxypropyl)-7-methylestr-4-en-3-one cyclic 1,2-ethanediyl dithioacetal (0.15 g) in dichloromethane (0.70 ml). After 3 h stirring at room temperature, solid sodium hydrogencarbonate (1 g), solid sodium thiosulfate (1 g), and water (5 ml) were added and the mixture was filtered. The product was extracted into ethyl acetate; the combined organic phases were washed with brine, dried over sodium sulfate and concentrated under reduced pressure. Column chromatography afforded [7α,14β,17α(S)]-17-(1-hydroxypropyl)-7-methylestr-4-en-3-one (0.069 g), $^1$H NMR (CDCl$_3$) δ 5.80 (m, 1H), 3.47 (m, 1H), 1.25 (s, 3H), 0.95 (t, 3H, J=7.4 Hz), 0.83 (d, 3H, J=7.0 Hz).

ivb)—Following a procedure analogous to that described under iva, [7α,14β,17α(R)]-17-(1-hydroxypropyl)-7-methylestr-4-en-3-one cyclic 1,2-ethanediyl dithioacetal (0.075 g) was converted to [7α,14β,17α(R)]-17-(1-hydroxypropyl)-7-methylestr-4-en-3-one (0.034 g), $^1$H NMR (CDCl$_3$) δ 5.80 (m, 1H), 3.66 (m, 1H), 1.07 (s, 3H), 0.95 (t, 3H, J=7.4 Hz), 0.85 (d, 3H, J=7.0 Hz).

EXAMPLE 18

In a manner analogous to the procedures described in Example 17, and using (7α,14β,17α)-17-formyl-7-methylestr-4-en-3-one cyclic 3-(1,2-ethanediyl dithioacetal) (Example 17, step ii) as starting material, the following products were prepared:

a)—[7α,14β,17α(S)]-17-(1-Hydroxy-2-propenyl)-7-methylestr-4-en-3-one.
$^1$H NMR (CDCl$_3$) δ 5.86 (m, 1H), 5.81 (m, 1H), 5.19 (dm, 1H, J=17.1 Hz), 5.07 (dm, 1H, J=10.3 Hz), 4.02 (m, 1H), 1.26 (s, 3H), 0.83 (d, 3H, J=7.0 Hz).

b)—[7α,14β,17α(R)]-17-(1-Hydroxy-2-propenyl)-7-methylestr-4-en-3-one.
$^1$H NMR (CDCl$_3$) δ 5.92 (m, 1H), 5.80 (m, 1H), 5.22 (dm, 1H, J=17.2 Hz), 5.11 (d, 1H, J=10.3 Hz), 4.10 (m, 1H), 1.07 (s, 3H), 0.84 (d, 3H, J=7.0 Hz).

c)—[7α,14β,17α(R)]-17-(1-Hydroxy-2-propynyl)-7-methylestr-4-en-3-one. $^1$H NMR (CDCl$_3$) δ 5.81 (m, 1H), 4.33 (m, 1H), 2.46 (d, 1H, J=2.0 Hz), 1.22 (s, 3H), 0.84 (d, 3H, J=7.1 Hz).

d)—[7α,14β,17α(S)]-17-(1-Hydroxy-2-propynyl)-7-methylestr-4-en-3-one.
$^1$H NMR (CDCl$_3$) δ 5.81 (m, 1H), 4.29 (m, 1H), 2.54 (d, 1H, J=2.0 Hz), 1.24 (s, 3H), 0.84 (d, 3H, J=7.1 Hz).

e)—(7α,14β,17α,20S)-20-Hydroxy-7-methyl-19,21-dinorchol-4-en-3-one.
$^1$H NMR (CDCl$_3$) δ 5.80 (m, 1H), 3.54 (m, 1H), 1.25 (s, 3H), 0.93 (t, 3H, J=7.2 Hz), 0.83 (d, 3H, J=7.0 Hz).

f)—(7α,14β,17α,20R)-20-Hydroxy-7-methyl-19,21-dinorchol-4-en-3-one.

$^1$H NMR (CDCl$_3$) δ 5.80 (m, 1H), 3.77 (m, 1H), 1.07 (s, 3H), 0.93 (t, 3H, J=7.1 Hz), 0.84 (d, 3H, J=7.0 Hz).

g)—(7α,14β,17α,20S)-20-Hydroxy-7-methyl-19,21-dinorchola-4,23-dien-3-one.

$^1$H NMR (CDCl$_3$) δ 5.87–5.79 (m, 2H), 5.20–5.14 (m, 2H), 3.56 (m, 1H), 1.25 (s, 3H), 0.83 (d, 3H, J=7.0 Hz).

h)—(7α,14β,17α,20R)-20-Hydroxy-7-methyl-19,21-dinorchola-4,23-dien-3-one.

$^1$H NMR (CDCl$_3$) δ 5.86–5.79 (m, 2H), 5.16–5.11 (m, 2H), 3.80 (m, 1H), 1.07 (s, 3H), 0.84 (d, 3H, J=7.0 Hz).

i)—(7α,14β,17α,20S)-20-Hydroxy-7-methyl-22,24-cyclo-19,21-dinorchol-4-en-3-one.

$^1$H NMR (CDCl$_3$) δ 5.80 (m, 1H), 2.81 (td, 1H, J=8.9 and 3.0 Hz), 1.25 (s, 3H), 0.89 (m, 1H), 0.83 (d, 3H, J=7.0 Hz), 0.57 (m, 1H), 0.44 (m, 1H), 0.32 (m, 1H), 0.22 (m, 1H).

j)—(7α,14β,17α,20R)-20-Hydroxy-7-methyl-22,24-cyclo-19,21-dinorchol-4-en-3-one.

$^1$H NMR (CDCl$_3$) δ 5.80 (m, 1H), 2.91 (dd, 1H, J=8.9 and 4.0 Hz), 1.08 (s, 3H), 1.00 (m, 1H), 0.85 (d, 3H, J=7.0 Hz), 0.55 (m, 2H), 0.33 (m, 1H), 0.25 (m, 1H).

k)—(7α,14β,17α,20R)-21,21,21-Trifluoro-20-hydroxy-7-methyl-19-norpregn4-en-3-one.

$^1$H NMR (CDCl$_3$) δ 5.81 (m, 1H), 3.89 (m, 1H), 1.28 (s, 3H), 0.84 (d, 3H, J=7.0 Hz).

l)—(7α,14β,17α,20S)-21,21,21-Trifluoro-20-hydroxy-7-methyl-19-norpregn-4-en-3-one.

$^1$H NMR (CDCl$_3$) δ 5.81 (m, 1H), 4.08 (m, 1H), 1.07 (s, 3H), 0.85 (d, 3H, J=7.0 Hz).

EXAMPLE 19

(7α,14β,17α)-20-Hydroxy-7,20-dimethyl-19-norpregn-4-en-3-one i)—Following a procedure analogous to that described under ii of Example 4, a mixture (1:1) of (7α,14β,17α,20S)-3-methoxy-7-methyl-19-norpregna-1,3,5(10)-trien-20-ol and (7α,14β,17α,20R)-3-methoxy-7-methyl-19-norpregna-1,3,5(10)-trien-20-ol (Example 16, step ii; 1.04 g) was converted to (7α,14β,17α)-3-methoxy-7-methyl-19-norpregna-1,3,5(10)-trien-20-one (0.85 g).

ii)—Following a procedure analogous to that described under ii of Example 16, the ketone obtained in the previous step (0.85 g) was converted to (7α,14β,17α)-3-methoxy-7,20-dimethyl-19-norpregna-1,3,5(10)-trien-20-ol (0.90 g).

iii)—Following a procedure analogous to that described under v of Example 4, the product obtained in the previous step (0.90 g) was converted to (7α,14β,17α)-3-methoxy-7,20-dimethyl-19-norpregna-2,5(10)-dien-20-ol (0.90 g).

iv)—Following a procedure analogous to that described under iv of Example 1, the product obtained in the previous step (0.90 g) was converted to (7α,14β,17α)-20-hydroxy-7,20-dimethyl-19-norpregn-4-en-3-one (0.45 g). M.p. 179–181° C.

EXAMPLE 20

In a manner analogous to the procedures described under ii of Example 16, v of Example 4, and iv of Example 1, respectively, and using (7α,14β,15β,16β,17α)-3-methoxy-7-methyl-15,16-methyleneestra-1,3,5(10)-triene-17-carboxaldehyde (Example 10, step iii) as starting material, the following products were prepared:

a)—(7α,14β,15β,16β,17α,20S)-20-Hydroxy-7-methyl-15,16-methylene-19-norpregn-4-en-3-one. M.p. 160–165° C.

b)—(7α,14β,15β,16β,17α,20R)-20-Hydroxy-7-methyl-15,16-methylene-19-norpregn-4-en-3-one. $[α]_D^{20}$=+61.2 (c=0.515, dioxane).

EXAMPLE 21

(7α,14β,15β,16β,17α)-20-Hydroxy-7,20-dimethyl-15,16-methylene-19-norpregn4-en-3-one The title compound was prepared from (7α,14β,15β,16β,17α)-3-methoxy-7-methyl-15,16-methyleneestra-1,3,5(10)-triene-17-carboxaldehyde (Example 10, step iii) in a manner analogous to the procedures described under ii of Example 16, v of Example 5, ii of Example 16, viii of Example 5, and iv of Example 1, respectively. M.p. 158.5–161.8° C.

4) 10-SUBSTITUTED COMPOUNDS

EXAMPLE 22

(14β,17α)-17-[(Acetyloxy)methyl]androst-4-en-3-one (a) and (14β,17α)-17-(Hydroxymethyl)androst-4-en-3-one (b)

i)—A solution of (3β)-3-(acetyloxy)androsta-5,14-dien-17-one [Andre, A. F. St. et al, J. Am. Chem. Soc. 74, 5506 (1952); 42.9 g] in dry ethanol (429 ml) was cooled to −10° C. Sodium borohydride (1.51 g) in dry ethanol (33.5 ml) was added and the mixture was stirred at −10° C. for 7.5 h. Excess sodium borohydride was destroyed by careful addition of an aqueous solution of acetic acid (50%). The product was extracted into ethyl acetate; the combined organic phases were washed with brine, dried over sodium sulfate and concentrated. Column chromatography provided (3β,17β)-androsta-5,14-diene-3,17-diol 3-acetate (19.5 g).

ii)—A solution of the product obtained in the previous step (20.0 g) in dry ethanol (500 ml), containing palladium on activated carbon (10%; 8.0 g), was stirred under hydrogen (3 bar) at room temperature for 16 h. The reaction mixture was filtered and the filtrate was concentrated under reduced pressure, to give (3β,14β,17β)-androst-5-ene-3,17-diol 3-acetate (20.2 g). The product was used in the following step without further purification.

iii)—Following a procedure analogous to that described under v of Example 5, the product obtained in the previous step (1.50 g) was converted to (3β,14β)-3-(acetyloxy)androst-5-en-17-one (1.08 g).

iv)—A solution of the ketone obtained in the previous step (1.08 g) in tetrahydrofuran (11.6 ml) and methanol (10.4 ml) was treated with a solution of potassium hydroxide (0.589 g) in water (3.51 ml). The reaction mixture was stirred overnight and then poured into brine. The product was extracted into ethyl acetate; the combined organic phases were washed with brine, dried over sodium sulfate and concentrated under reduced pressure, to give (3β,14β)-3-hydroxyandrost-5-en-17-one (1.06 g). The product was used in the next step without further purification.

v)—Following a procedure analogous to that described under iii of Example 5, the alcohol obtained in the previous step (1.06 g) was converted to (3β,14β)-3-[[(1,1-dimethylethyl)dimethylsilyl]oxy]androst-5-en-17-one (1.70 g).

vi)—Following a procedure analogous to the procedure described under iii of Example 4, the ketone obtained in the previous step (1.70 g) was converted to (3β,14β)-3-[[(1,1-dimethylethyl)dimethylsilyl]oxy]-17-methyleneandrost-5-ene (1.41 g).

vii)—Following a procedure analogous to the procedure described under iv of Example 4, the product obtained in the previous step (1.41 g) was converted to (3β,14β,17α)-3-[[(1,1-dimethylethyl)dimethylsilyl]oxy]androst-5-ene-17-methanol (2.28 g).

viii)—A solution of the alcohol obtained in the previous step (2.28 g) in dry pyridine (3.38 ml) was treated with acetic anhydride (1.74 ml) and the mixture was stirred at room temperature for 1 h. Water was added and stirring was continued for another 1 h. The product was extracted into ethyl acetate; the combined organic phases were washed with a saturated aqueous solution of sodium hydrogencarbonate and brine, dried over sodium sulfate and concentrated under reduced pressure, to give (3β,14β,17α)-3-[[(1,1-dimethylethyl)dimethylsilyl]oxy]-17-[(acetyloxy)methyl]androst-5-ene (1.43 g). The product was used in the next step without further purification.

ix)—Following a procedure analogous to the procedure described under iv of Example 1, the product obtained in the previous step (1.43 g) was converted to (3β,14β,17α)-17-[(acetyloxy)methyl]androst-5-en-3-ol (0.78 g).

x)—A mixture of the product obtained in the previous step (0.774 g) and aluminium isopropoxide (0.64 g) in dry toluene (9.2 ml) and 2-butanone (5.6 ml) was heated under reflux for 1 h. After cooling, a solution of potassium sodium tartrate tetrahydrate (4.4 g) in water (6 ml) was added and the mixture was stirred at room temperature for 30 min. The product was extracted into ethyl acetate; the combined organic phases were washed with water and brine, dried over sodium sulfate and concentrated under reduced pressure. Column chromatography afforded (14β,17α)-17-[(acetyloxy)methyl]androst-4-en-3-one (0.44 g), m.p. 141–142° C.

xi)—Following a procedure analogous to that described under iv, (14β,17α)-17-[(acetyloxy)methyl]androst-4-en-3-one (0.32 g) was converted to (14β,17α)-17-(hydroxymethyl)androst-4-en-3-one (0.10 g), m.p. 125.1–127.6° C.

5) 15-SUBSTITUTED COMPOUNDS

EXAMPLE 23

(14β,15β,17α)-17-(Hydroxymethyl)-15-methylestr-4-en-3-one

Following procedures analogous to those described under v–ix of Example 7, (14β,15β,17α)-17-(hydroxymethyl)-15-methylestr-4-en-3-one was prepared from (14β)-3-methoxyestra-1,3,5(10),15-tetraen-17-one [Johnson, J. et al, J. Amer. Chem. Soc. 79, 2005 (1957)]. $[\alpha]_D^{20}$=+3.9 (c 1.20, dioxane).

6) 20-SUBSTITUTED COMPOUNDS

EXAMPLE 24

(14β,17α,20S)-20-Hydroxy-19-norpregn-4-en-3-one (a) and (14β,17α,20R)-20-Hydroxy-19-norpregn-4-en-3-one (b)

i)—A solution of sulfur trioxide pyridine complex (50.0 g) in dimethyl sulfoxide (250 ml) was added in 15 min. to a solution of (14β,17α)-3-methoxyestra-1,3,5(10)-triene-17-methanol (Example 1, step ii; 23.6 g) in a mixture of dimethyl sulfoxide (425 ml) and triethylamine (70 ml). After 20 min. stirring, 2-propanol (88 ml) was added and stirring was continued for 15 min. The reaction mixture was poured into water (1300 ml) and the product was extracted into dichloromethane. The combined organic phases were washed with water and brine, dried over magnesium sulfate and concentrated under reduced pressure. Trituration (water/ethanol, first 3:2, then 1:1) afforded (14β,17α)-3-methoxyestra-1,3,5(10)-triene-17-carboxaldehyde (18.8 g).

ii)—Following a procedure analogous to that described under ii of Example 16, the product obtained in the previous step (3.5 g) was converted to (14β,17α,20S)-3-methoxy-19-norpregna-1,3,5(10)-trien-20-ol (1.78 g) and (14β,17α,20R)-3-methoxy-19-norpregna-1,3,5(10)-trien-20-ol (1.16 g).

iiia)—Following a procedure analogous to that described under iii of Example 1, (14β,17α,20S)-3-methoxy-19-norpregna-1,3,5(10)-trien-20-ol (1.5 g) was converted to (14β,17α,20S)-3-methoxy-19-norpregna-2,5(10)-dien-20-ol (1.59 g).

iiib)—Following a procedure analogous to that described above, (14β,17α,20R)-3-methoxy-19-norpregna-1,3,5(10)-trien-20-ol (1.0 g) was converted to (14β,17α,20R)-3-methoxy-19-norpregna-2,5(10)-dien-20-ol (1.13 g).

iva)—Following a procedure analogous to that described under iv of Example 1, (14β,17α,20S)-3-methoxy-19-norpregna-2,5(10)-dien-20-ol (1.42 g) was converted to (14β,17α,20S)-20-hydroxy-19-norpregn-4-en-3-one (0.84 g), m.p. 152–153° C.

ivb)—Following a procedure analogous to that described above, (14β,17α,20R)-3-methoxy-19-norpregna-2,5(10)-dien-20-ol (1.13 g) was converted to (14β,17α,20R)-20-hydroxy-19-norpregn-4-en-3-one (0.72 g), m.p. 108–109.5° C.

EXAMPLE 25

In a manner analogous to the procedures described in Example 24, and using (14β,17α)-3-methoxyestra-1,3,5 (10)-triene-17-carboxaldehyde (Example 24, step i) as starting material, the following products were prepared:

a)—[14β,17α(S)-17-(1-Hydroxypropyl]estr-4-en-3-one. M.p. 122–123° C.

b)—[14β,17α(R)]-17-(1-Hydroxypropyl)estr-4-en-3-one. M.p. 120–121° C.

c)—(14β,17α,20S)-20-Hydroxy-19,21-dinorchol-4-en-3-one. M.p. 102–102.5° C.

d)—(14β,17α,20R)-20-Hydroxy-19,21-dinorchol4-en-3-one.

$^1$H NMR δ 5.81 (m, 1H), 3.76 (m, 1H), 1.08 (s, 3H), 0.92 (t, 3H, J=7.0 Hz).

EXAMPLE 26

In a manner analogous to the procedures described in Example 17, and using (14β,17α)-17-(hydroxymethyl)estr-4-en-3-one (Example 1) as starting material, the following products were prepared:

a)—[14β,17α(R)]-17-(1-Hydroxy-2-propynyl)estr-4-en-3-one.

$^1$H NMR (CDCl$_3$) δ 5.82 (m, 1H), 4.34 (m, 1H), 2.46 (d, 1H, J=2.0 Hz), 1.21 (s, 3H).

b)—[14β,17α(S)]-17-(1-Hydroxy-2-propynyl)estr-4-en-3-one.

$^1$H NMR (CDCl$_3$) δ 5.82 (m, 1H), 4.29 (m, 1H), 2.54 (d, 1H, J=2.4 Hz), 1.24 (s, 3H), c)—(14β,17α,20R)-21,21,21-Trifluoro-20-hydroxy-19-norpregn-4-en-3-one.

$^1$H NMR (CDCl$_3$) δ 5.83 (m, 1H), 3.91 (m, 1H), 1.27 (s, 3H).

d)—(14β,17α,20S)-21,21,21-Trifluoro-20-hydroxy-19-norpregn-4-en-3-one.

$^1$H NMR (CDCl$_3$) δ 5.83 (m, 1H), 4.09 (m, 1H), 1.07 (s, 3H).

e)—[14β,17α(R)]-17-[(Hydroxy)(phenyl)methyl]estr-4-en-3-one.

$^1$H NMR (CDCl$_3$) δ 7.34 (m, 4H), 7.29 (m, 1H), 5.81 (m, 1H), 4.65 (dd, 1H, J=6.7 and 3.1 Hz), 0.61 (s, 3H).

f)—[14β,17α(S)]-17-[(Hydroxy)(phenyl)methyl]estr-4-en-3-one.

$^1$H NMR (CDCl$_3$) δ 7.33 (m, 4H), 7.27 (m, 1H), 5.82 (m, 1H), 4.55 (dd, 1H, J=10.2 and 3.5 Hz), 1.36 (s, 3H).

EXAMPLE 27

(14β,17α,20S)-20-Hydroxy-19-norpregna-4,9-dien-3-one (a) and (14β,17α,20R)-20-Hydroxy-19-norpregna-4,9-dien-3-one (b)

i)—Following a procedure analogous to that described for Example 2, a mixture of (14β,17α,20S)-3-methoxy-19-norpregna-2,5(10)-dien-20-ol and (14β,17α,20R)-3-methoxy-19-norpregna-2,5(10)-dien-20-ol (Example 24, step iiia and iiib, respectively; ratio 1:1; 7.87 g) was converted to a mixture of (14β,17α,20S)-20-hydroxy-19-norpregn-5(10)-en-3-one and (14β,17α,20R)-20-hydroxy-19-norpregn-5(10)-en-3-one (7.5 g; ratio 1:1).

ii)—Following a procedure analogous to that described in Example 3, the mixture obtained in the previous step (7.5 g) was converted to (14β,17α,20S)-20-hydroxy-19-norpregna-4,9-dien-3-one (2.4 g), m.p. 147–148° C., and (14β,17α,20R)-20-hydroxy-19-norpregna-4,9-dien-3-one (1.95 g), m.p. 118–119° C.

7) 11,20-SUBSTITUTED COMPOUNDS

EXAMPLE 28

(11β,14β,17α,20S)-11-Ethyl-20-hydroxy-19-norpregn-5(10)-en-3-one (a) and (11β,14β,17α,20R-11-Ethyl-20-hydroxy-19-norpregn-5(10)-en-3-one (b)

i)—A solution of (11β)-11-ethyl-3-methoxyestra-1,3,5(10)-trien-17-one [Pomper, M. G. et al, J. Med. Chem. 33, 3143 (1990); 15 g] in a mixture of tetrahydrofuran (50 ml), ethylene glycol (30 ml), and triethyl orthoformate (30 ml) was treated with p-toluenesulfonic acid (0.25 g) and the reaction mixture was stirred at room temperature overnight. Sodium hydrogencarbonate (1 g) was added and after 10 min. stirring the mixture was concentrated under reduced pressure. Then it was poured into an aqueous solution of sodium hydrogencarbonate (5%, 200 ml) and the product was extracted into ethyl acetate. The combined organic phases were washed with brine, dried over sodium sulfate and concentrated under reduced pressure. Column chromatography afforded (11β)-1-ethyl-3-methoxyestra-1,3,5(10)-trien-17-one cyclic 1,2-ethanediyl acetal (16.2 g).

ii)—Following a procedure analogous to that described under ii of Example 7, the product obtained in the previous step (16.0 g) was converted to (11β,16α)-16-bromo-11-ethyl-3-methoxyestra-1,3,5(10)-trien-17-one cyclic 1,2-ethanediyl acetal (18.5 g).

iii)—Following a procedure analogous to that described under iii of Example 7, the bromide obtained in the previous step (18.0 g) was converted to (11β)-11-ethyl-3-methoxyestra-1,3,5(10),15-tetraen-17-one cyclic 1,2-ethanediyl acetal (13.0 g).

iv)—Following a procedure analogous to that described under iv of Example 7, the product obtained in the previous step (13.0 g) was converted to (11β)-11-ethyl-3-methoxyestra-1,3,5(10),15-tetraen-17-one (7.6 g).

v)—A solution of the ketone obtained in the previous step (8.5 g) and p-toluenesulfonic acid (0.20 g) in isopropenyl acetate (75 ml) was heated under reflux for 30 min. The reaction medium was partially (25 ml) distilled off and replaced by fresh isopropenyl acetate (25 ml). Heating was continued for another 30 min., an aqueous solution of sodium hydrogencarbonate (10%) was added, and the mixture was concentrated. The product was extracted into diethyl ether, the combined organic phases were washed with brine, dried over sodium sulfate and concentrated under reduced pressure. The residue was taken up in a mixture of tetrahydrofuran (75 ml), ethanol (75 ml) and water (10 ml). Sodium borohydride (2 g) was added and the mixture was stirred at room temperature for 1 h. Excess sodium borohydride was destroyed by careful addition of acetone (25 ml). The mixture was concentrated, water was added and the product was extracted into ethyl acetate. The combined organic phases were washed with brine, dried over sodium sulfate and concentrated. Column chromatography provided (11β,17β)-11-ethyl-3-methoxyestra-1,3,5(10),14-tetraen-17-ol (8.0 g).

vi)—A mixture of the product obtained in the previous step (6.2 g) and palladium on activated carbon (5%; 1.0 g) in ethanol (100 ml) was stirred under hydrogen (1 bar) at room temperature for 24 h. The reaction mixture was filtered and the filtrate was concentrated under reduced pressure, to give (11β,14β,17β)-11-ethyl-3-methoxyestra-1,3,5(10)-trien-17-ol (6.0 g). The product was used in the following step without further purification.

vii)—Following a procedure analogous to that described under i of Example 16, the product obtained in the previous step (6.0 g) was converted to (11β,14β)-11-ethyl-3-methoxyestra-1,3,5(10)-trien-17-one (4.7 g).

viii)—Following a procedure analogous to that described under iii of Example 4, the product obtained in the previous step (1.0 g) was converted to (11β,14β)-11-ethyl-3-methoxy-17-methyleneestra-1,3,5(10)-triene (1.0 g).

ix)—Following a procedure analogous to that described under iv of Example 4, the product obtained in the previous step (4.0 g) was converted to (11β,14β,17α)-11-ethyl-3-methoxyestra-1,3,5(10)-triene-17-methanol (3.5 g).

x)—Following a procedure analogous to that described under iii of Example 1, the product obtained in the previous step (3.2 g) was converted to (11β,14β,17α)-11-ethyl-3-methoxyestra-2,5(10)-diene-17-methanol (3.3 g).

xi)—A solution of (11β,14β,17α)-11-ethyl-3-methoxyestra-2,5(10)-diene-17-methanol (3.3 g) in tetrahydrofuran (30 ml) was treated with hydrochloric acid (2 M, 10 ml). The reaction mixture was stirred at room temperature for 30 min. and then neutralized with a saturated aqueous solution of sodium hydrogencarbonate. Water was added and the product was extracted into ethyl acetate. The combined organic phases were washed with brine, dried over sodium sulfate and concentrated under reduced pressure, to give (11β,14β,17α)-11-ethyl-17-(hydroxymethyl)estr-5(10)-en-3-one (3.3 g). The product was used in the following step without further purification.

xii)—A solution of the ketone obtained in the previous step (3.3 g) and p-toluenesulfonic acid (0.1 g) in methanol (30 ml) and trimethyl orthoformate (6 ml) was stirred at room temperature for 15 min. Solid sodium hydrogencarbonate (1 g) was added and stirring was continued for another 15 min. The reaction mixture was partially concentrated, an aqueous solution of sodium hydrogencarbonate (5%) was added and the product was extracted into ethyl acetate. The combined organic phases were washed with brine, dried over sodium sulfate and concentrated under reduced pressure. Column chromatography provided (11β,14β,17α)-11-ethyl-3,3-dimethoxyestr-5(10)-ene-17-methanol (3.0 g).

xiii)—A solution of oxalyl chloride (1 ml) in dichloromethane (60 ml) was cooled to −60° C. Dimethyl sulfoxide (1.64 ml) was added and the mixture was stirred for 5 min. A solution of the compound obtained in the previous step (2.6 g) in dichloromethane (5 ml) was added and stirring was continued for 20 min. Triethylamine (5 ml) was added and the temperature was allowed to rise to 0° C. in 20 min. Water (50 ml) was added and the product was extracted into diethyl ether. The combined organic phases were washed with brine, dried over sodium sulfate and concentrated under reduced pressure. Column chromatography afforded (11β,17α)-11-ethyl-3,3-dimethoxyestr-5(10)-ene-17-carboxaldehyde (2.4 g).

xiv)—Following a procedure analogous to that described under ii of Example 16, the product obtained in the previous step (2.4 g) was converted to (11β,14β,17α,20S)-11-ethyl-3,3-dimethoxy-19-norpregn-5(10)-en-20-ol (1.25 g) and (11β,14β,17α,20R)-11-ethyl-3,3-dimethoxy-19-norpregn-5(10)-en-20-ol (0.90 g).

xva)—A solution of (11β,14β,17α,20S)-11-ethyl-3,3-dimethoxy-19-norpregn-5(10)-en-20-ol (1.25 g) in tetrahydrofuran (12 ml) was treated with hydrochloric acid (0.6 M, 2 ml). The reaction mixture was stirred at room temperature for 30 min. and then neutralized with a saturated aqueous solution of sodium hydrogencarbonate. Water was added and the product was extracted into ethyl acetate. The combined organic phases were washed with brine, dried over sodium sulfate and concentrated tinder reduced pressure. Crystallization gave (11β,14β,17α,20S)-11-ethyl-20-hydroxy-19-norpregn-5(10)-en-3-one (0.85 g), m.p. 177–178° C.

xvb)—Following a procedure analogous to that described under xva, (11β,14β,17α,20R)-11-ethyl-3,3-dimethoxy-19-norpregn-5(10)-en-20-ol (0.90 g) was converted to (11β,14β,17α,20R)-11-ethyl-20-hydroxy-19-norpregn-5(10)-en-3-one (0.68 g), $^1$H NMR δ 3.89 (m, 1H), 2.77 (m, 2H), 1.26 (d, 3H, J=6.2 Hz), 1.18 (s, 3H), 0.89 (t, 3H, J 6.8 Hz).

EXAMPLE 29

In a manner analogous to the procedure described under iv of Example 1, the following products were prepared:

a)—(11β,14β,17α,20S)-11-Ethyl-20-hydroxy-19-norpregn-4-en-3-one from (11β,14β,17α,20S)-11-ethyl-20-hydroxy-19-norpregn-5(10)-en-3-one (Example 28a). $[α]_D^{20}$=+82.4° (c=0.71, dioxane).

b)—(11β,14β,17α,20R)-11-Ethyl-20-hydroxy-19-norpregn-4-en-3-one from (11β,14β,17α,20R)-11-ethyl-20-hydroxy-19-norpregn-5(10)-en-3-one (Example 28b). M.p. 185–186° C.

EXAMPLE 30

(11β,14β,17α,20S)-11-Ethenyl-20-hydroxy-19-norpregna-4,9-dien-3-one i)—Following a procedure analogous to that described under i of Example 28, (14β,17α,20S)-20-hydroxy-19-norpregna-4,9-dien-3-one (Example 27a; 2.5 g) was converted to (14β,17α,20S)-20-hydroxy-19-norpregna-5(10),9(11)-dien-3-one cyclic 1,2-ethanediyl acetal ii)—A solution of the product obtained in the previous step (1.5 g) in dry dichloromethane (15 ml), containing sodium hydrogencarbonate (3 g), was cooled to −15° C. m-Chloroperbenzoic acid (60%, 1.42 g) in dry dichloromethane (12.5 ml) was added in 10 min. and the reaction mixture was stirred at −10° C. for 1.25 h. Then it was poured into a mixture of a saturated aqueous solution of sodium hydrogencarbonate (53 ml) and an aqueous solution of sodium hydrogensulfite (5%, 12.5 ml) and the product was extracted into dichloromethane. The combined organic phases were washed with a saturated aqueous solution of sodium hydrogencarbonate, water and brine, dried over sodium sulfate and concentrated under reduced pressure, to give (5α,10α,14β,17α,20S)-5,10-epoxy-20-hydroxy-19-norpregn-9(11)-en-3-one cyclic 1,2-ethanediyl acetal (1.6 g).

iii)—A solution of the epoxide obtained in the previous step (1.6 g) in dry tetrahydrofuran (15 ml), containing copper(I) chloride (0.20 g), was cooled to 0° C. and treated with a solution of vinylmagnesium bromide in tetrahydrofuran (15%, 12.7 ml). After 1 h stirring at 0° C. the reaction mixture was poured into an aqueous solution of ammonium chloride (10%). The product was extracted into dichloromethane; the combined organic phases were washed with water and brine, dried over sodium sulfate and concentrated under reduced pressure. Column chromatography afforded (5α,11β,14β,17α,20S)-11-ethenyl-5,20-dihydroxy-19-norpregn-9-en-3-one cyclic 1,2-ethanediyl acetal (0.65 g).

iv)—Following a procedure analogous to that descibed under iv of Example 1, the product obtained in the previous step (0.60 g) was converted to (11β,14β,17α,20S)-11-ethenyl-20-hydroxy-19-norpregna-4,9-dien-3-one (0.28 g), m.p. 144.5–146.1° C.

EXAMPLE 31

(11β,14β,17α,20R-11-Ethenyl-20-hydroxy-19-norpregna-4,9-dien-3-one

In a manner analogous to the procedures described in Example 30, (14β,17α,20R)-20-hydroxy-19-norpregna-4,9-dien-3-one (Example 27b) was converted to (11β,14β,17α,20R)-11-ethenyl-20-hydroxy-19-norpregna-4,9-dien-3-one. M.p. 96.3–97.2° C.

8) 18,20-SUBSTITUTED COMPOUNDS

EXAMPLE 32

Following procedures analogous to those described in Example 4 and 16, respectively, and using (17β)-13-ethyl-3-methoxygona-1,3,5(10),14-tetraen-17-ol [U.S. Pat. No. 3,577,410 (1968)] as starting material, the following products were prepared:

a)—(14β,17α,20S)-13-Ethyl-20-hydroxy-18,19-dinorpregn-4-en-3-one. $[α]_D^{20}$=+78.3 (c=0.36, dioxane).

b)—(14β,17α,20R)-13-Ethyl-20-hydroxy-18,19-dinorpregn-4-en-3-one. M.p. 110.5–111.5° C.

c)—[14β,17α(S)]-13-Ethyl-17-(1-hydroxypropyl)gon-4-en-3-one.

$[α]_D^{20}$=+64.1° (c=0.34, dioxane).

d)—[14β,17α(R)]-13-Ethyl-17-(1-hydroxypropyl)gon-4-en-3-one. M.p. 89.5–90.5° C.

e)—[14β,17α(S)]-13-Ethyl-17-(1-hydroxy-2-propenyl)gon-4-en-3-one.

¹H NMR δ 5.96–5.76 (m, 2H), 5.25–5.01 (m, 2H), 4.02 (m, 1H), 0.89 (t, 3H, J=8.0 Hz).

f)—[14β,17α(R)]-13-Ethyl-17-(1-hydroxy-2-propenyl)gon-4-en-3-one. M.p. 128.5–129.5° C.

9) MISCELLANEOUS

EXAMPLE 33

Following a procedure analogous to that described under viii of Example 22, using (7α,14β,17α)-17-(hydroxymethyl)-7-methylestr-4-en-3-one (Example 4) as starting material, the following products were prepared:

a)—(7α,14β,17α)-17-[(Acetyloxy)methyl]-7-methylestr-4-en-3-one. M.p. 65–68° C.

b)—(7α,14β,17α)-17-[[(2,2-Dimethyl-1-oxopropyl)oxy]methyl]-7-methylestr4-en-3-one.

¹H NMR δ 5.81 (m, 1H), 4.12 (m, 1H), 3.95 (m, 1H), 1.20 (s, 9H), 1.12 (s, 3H), 0.84 (d, 3H,J=7.4Hz).

c)—(7α,14β,17α)-7-Methyl-17-[[(1-oxoundecyl)oxy]methyl]estr-4-en-3-one. M.p. 45.5–48.5° C.

d)—(7α,14β,17α)-17-[[[(trans-4-Butylcyclohexyl)carbonyl]oxy]methyl]-7-methylestr-4-en-3-one. [α]$_D^{20}$=+63.1 (c=0.635, dioxane).

e)—(7α,14β,17α)-7-Methyl-17-[[(phenylcarbonyl)oxy]methyl]estr-4-en-3-one.

¹H NMR δ 8.03 (m, 2H), 7.56 (m, 1H), 7.44 (m, 2H), 5.81 (m, 1H), 4.40 (m, 1H), 4.22 (m, 1H), 1.18 (s, 3H), 0.85 (d, 3H, J=7.1 Hz).

EXAMPLE 34

(3β,7α,14β,17α)-17-(Hydroxymethyl)-7-methylestr-4-en-3-ol

Following a procedure analogous to that described under ix of Example 6, the title compound was prepared from (7α,14β,17α)-17-(hydroxymethyl)-7-methylestr-4-en-3-one (Example 4). [α]$_D^{20}$=+28.2° (c=0.49, dioxane).

EXAMPLE 35

(3α,7α,14β,17α)-17-(Hydroxymethyl)-7-methylestr-5(10)-en-3-ol

The title compound (2.27 g) was isolated as side product after Birch reduction and hydrolysis of (7α,14β,17α)-3-methoxy-7-methylestra-1,3,5(10)-triene-17-methanol (Example 4, step iv; 22.0 g). M.p. 64–70° C.

EXAMPLE 36

(3E,7α,14β,17α)-3-(Hydroxyimino)-7-methylestr-4-ene-17-methanol (a) and (3Z,7α,14β,17α)-3-(Hydroxyimino)-7-methylestr-4-ene-17-methanol (b)

To a solution of (7α,14β,17α)-17-(hydroxymethyl)-7-methylestr4-en-3-one (Example 4; 1.0 g) in pyridine (6 ml) was added hydroxylamine hydrochloride (2.65 g). The reaction mixture was stirred at 80° C. for 1.5 h. After cooling, the mixture was poured into water. The product was extracted into ethyl acetate; the combined organic phases were washed with brine, dried over sodium sulfate and concentrated under reduced pressure. Column chromatography afforded (3E,7α,14β,17α)-3-(hydroxyimino)-7-methylestr-4-ene-17-methanol (0.54 g), [α]$_D^{20}$=+95.5 ° (c=1.41, dioxane), and (3Z,7α,14β,17α)-3-(hydroxyimino)-7-methylestr-4-ene-17-methanol(0.28 g), [α]$_D^{20}$=+87.4 (c=1.0, dioxane).

EXAMPLE 37

(7α,14β,17α)-7-Methylestr4-ene-17-methanol (7α,14β,17α)-17-(Hydroxymethyl)-7-methylestr-4-en-3-one cyclic 1,2-ethanediyl dithioacetal (Example 17, step i; 1.11 g) in dry tetrahydrofuran (4 ml) was added to a solution of sodium (0.61 g) in liquid ammonia (70 ml), cooled to −40° C. After 1 h stirring, dry ethanol was added and the ammonia was allowed to evaporate. Water was added and the product was extracted into ethyl acetate. The combined organic phases were washed with aqueous sodium hydroxide (1 M), water and brine, dried over magnesium sulfate and concentrated under reduced pressure. Column chromatography afforded (7α,14β,17α)-7-methylestr-4-ene-17-methanol (0.34 g), [α]$_D^{20}$=+56.9 ° (c=0.93, dioxane).

Results

A plurality of compounds according to the invention were tested for androgenic activity (the procedures for which have been described above) and rated in the Table below according to the following scheme:

+ androgenic activity found;

++ high androgenic activity;

+++ excellent androgenic activity;

nd no data available

Parent compound of the compounds of the invention is (14β,17α)-17-(hydroxymethyl)estr-4-en-3-one (Example 1). Compounds in the Table are derivatives of the latter; they all have a carbonyl group at C-3 and a Δ⁴ double bond unless otherwisely stated.

TABLE

Androgenic activities of compounds of the invention.

| Example | | Rating | Example | Rating |
|---|---|---|---|---|
| Unsubstituted | | | 20-Substituted | |
| 1 | | +++ | 24a  20S-Me | ++ |
| 2 | Δ$^{5(10)}$ | ++ | 24b  20R-Me | + |
| 3 | Δ$^{4.9}$ | + | 25a  20S-Et | ++ |
| | | | 25b  20R-Et | + |
| 7-Substituted | | | 25c  20S-Pr | + |
| 4 | 7α-Me | +++ | 25d  20R-Pr | nd |
| 5 | 7α-Me, Δ$^{4.15}$ | +++ | 26a  20R-ethynyl | nd |
| 6 | 7α-Me, 14β-Me | ++ | 26b  20S-ethynyl | nd |
| 7 | 7α-Me, 15β-Me | + | 26c  20R-CF$_3$ | nd |
| 8 | 7α-Me, 16α-Me | + | 26d  20S-CF$_3$ | nd |
| 9 | 7α-Me, 16β-Me | ++ | 26e  20R-Ph | nd |
| 10 | 7α-Me, 15β, 16β-CH$_2$ | ++ | 26f  20S-Ph | nd |
| 11 | 7α-Me, 17β-Me | + | 27a  Δ$^{4.9}$, 20S-Me | ++ |
| 12 | 7α-Me, 17β-F | +++ | 27b  Δ$^{4.9}$, 20R-Me | + |
| 13 | 7α-Me, 17β-OH | + | | |
| 14 | 7α-Et | + | 11, 20-Substituted | |
| 15 | 7α-Vinyl | ++ | 28a  Δ$^{5(10)}$, 11β-Et, 20S-Me | + |
| | | | 28b  Δ$^{5(10)}$, 11β-Et, 20R-Me | nd |
| 7, 20-Substituted | | | 29a  11β-Et, 20S-Me | + |
| 16a | 7α-Me, 20S-Me | ++ | 29b  11βEt, 20S-Me | + |
| 16b | 7α-Me, 20R-Me | + | 30  Δ$^{4.9}$, 11β-vinyl, 20S-Me | + |
| 17a | 7α-Me, 20S-Et | nd | 31  Δ$^{4.9}$, 11β-vinyl, 20R-Me | + |
| 17b | 7α-Me, 20R-Et | + | | |
| 18a | 7α-Me, 20S-vinyl | + | 18, 20-Substituted | |
| 18b | 7α-Me, 20R-vinyl | + | 32a  18-Me, 20S-Me | + |

TABLE-continued

Androgenic activities of compounds of the invention.

| Example | | Rating | Example | | Rating |
|---|---|---|---|---|---|
| 18c | 7α-Me, 20R-ethynyl | + | 32b | 18-Me, 20R-Me | + |
| 18d | 7α-Me, 20S-ethynyl | + | 32c | 18-Me, 20S-Et | nd |
| 18e | 7α-Me, 20S-Pr | nd | 32d | 18-Me, 20R-Et | nd |
| 18f | 7α-Me, 20R-Pr | nd | 32e | 18-Me, 20S-vinyl | nd |
| 18g | 7α-Me, 20S-allyl | + | 32f | 18-Me, 20R-vinyl | nd |
| 18h | 7α-Me, 20R-allyl | + | Miscellaneous | | |
| 18i | 7α-Me, 20S-cyclopropyl | nd | | | |
| 18j | 7α-Me, 20R-cyclopropyl | nd | 33a | 7α-Me, acetate | + |
| 18k | 7α-Me, 20R-CF$_3$ | nd | 33b | 7α-Me, diMepropionate | nd |
| 18l | 7α-Me, 20S-CF$_3$ | nd | 33c | 7α-Me, undecanoate | + |
| 19 | 7α-Me, 20, 20-diMe | + | 33d | 7α-Me, buciclate | + |
| 20a | 7α-Me, 15β, 16β-CH$_2$, 20S-Me | ++ | 33e | 7α-Me, benzoate | nd |
| 20b | 7α-Me, 15β, 16β-CH$_2$, 20R-Me | + | 34 | 7α-Me, 3β-OH | ++ |
| 21 | 7α-Me, 15β, 16β-CH$_2$, 20, 20-diMe | + | 35 | Δ$^{5(10)}$, 7α-Me, 3α-OH | nd |
| | | | 36a | 7α-Me, 3E-(NOH) | + |
| 10-Substituted and 15-Substituted | | | 36a | 7α-Me, 3Z-(NOH) | + |
| 22a | 10-Me, acetate | + | 37 | 7α-Me, 3, 3-diH | + |
| 22b | 10-Me | + | | | |
| 23 | 15β-Me | + | | | |

What is claimed is:

1. A steroid compound satisfying the structural formula:

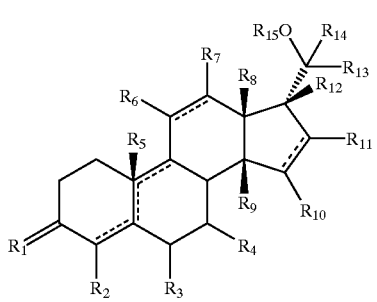

Formula I wherein

R$_1$ is O, (H,H), (H,OR), NOR, with R being hydrogen, (C$_{1-6}$)alkyl, (C$_{1-6}$)acyl;

R$_2$ is hydrogen, (C$_{1-6}$)alkyl, or halogen;

R$_3$ is hydrogen, (C$_{1-6}$)alkyl, (C$_{2-6}$)alkenyl, or (C$_{2-6}$)alkynyl;

R$_4$ is hydrogen, halogen, or cyano; or R$_4$ is (C$_{1-6}$)alkyl, (C$_{2-6}$)alkenyl or (C$_{2-6}$)alkynyl, each optionally substituted by hydroxy, (C$_{1-4}$)alkoxy, oxo, halogen, or cyano;

R$_5$ is hydrogen, or (C$_{1-6}$)alkyl;

R$_6$ is hydrogen, (C$_{1-6}$)alkoxy, or halogen; or R$_6$ is (C$_{1-6}$)alkyl, (C$_{2-6}$)alkenyl, (C$_{2-6}$)alkynyl, a (C$_{1-6}$)alkylidene group, or a (C$_{2-6}$)alkenylidene group, each optionally substituted by hydroxy, (C$_{1-4}$)alkoxy, oxo, halogen, or cyano;

R$_7$ is hydrogen, or (C$_{1-6}$)alkyl;

R$_8$ is (C$_{1-4}$)alkyl;

R$_9$ is hydrogen, halogen or cyano; or R$_9$ is (C$_{1-6}$)alkyl, (C$_{2-6}$)alkenyl, or (C$_{2-6}$)alkynyl, each optionally substituted by hydroxy, (C$_{1-4}$)alkoxy, oxo, halogen, or cyano;

R$_{10}$ is hydrogen, (C$_{1-6}$)alkoxy, halogen, or cyano; or R$_{10}$ is (C$_{1-6}$)alkyl, (C$_{2-6}$)alkenyl or (C$_{2-6}$)alkynyl, each optionally substituted by hydroxy, (C$_{1-4}$)alkoxy, oxo, halogen, or cyano; or R$_{10}$ together with R$_{11}$ and the carbon atoms at which they are placed form a cyclopropane ring;

R$_{11}$ is hydrogen, (C$_{1-6}$)alkoxy, halogen, or cyano; or R$_{11}$ is (C$_{1-6}$)alkyl, (C$_{2-6}$)alkenyl or (C$_{2-6}$)alkynyl, each optionally substituted by hydroxy, (C$_{1-4}$)alkoxy, oxo, halogen, or cyano; or R$_{11}$ together with R$_{10}$ and the carbon atoms at which they are placed form a cyclopropane ring;

R$_{12}$ is hydrogen, hydroxy, halogen, or cyano; or R$_{12}$ is (C$_{1-6}$)alkyl, (C$_{2-6}$)akenyl, (C$_{2-6}$)alknyl, each optionally substituted by hydroxy, (C$_{1-4}$)alkoxy, oxo, halogen, or cyano;

R$_{13}$ and R$_{14}$ are independently hydrogen, cyano, or phenyl, the latter optionally substituted by hydroxy, (C$_{1-4}$)alkoxy, (C$_{1-4}$)alkyl or halogen; or R$_{13}$ and R$_{14}$ are independently (C$_{1-6}$)alkyl, (C$_{2-6}$)alkenyl, (C$_{3-6}$)cycloalkyl, (C$_{5-6}$)cycloalkenyl or (C$_{2-6}$) alkynyl, each optionally substituted by hydroxy, (C$_{1-4}$)alkoxy, phenyl, oxo, halogen, or cyano; or R$_{13}$ and R$_{14}$ together with the carbon atom at which they are placed form a (C$_{3-6}$)cycloalkene ring or a (C$_{5-6}$)cycloalkene ring;

R$_{15}$ is hydrogen, SO$_3$H, (C$_{1-6}$)alkyl, (C$_{1-15}$)acyl; and the dotted lines indicate optional bonds, with the proviso that the compound is not any one of 20-hydroxy-14β, 17α-19-norpregn-4en-3one, (3β,5α,14β,17α)-pregna-3,20-diol, (3β,14β,17α)-pregna-5,9(11)dien-3,20-diol, (14β,17α)-20hydroxy-19-norpregn-4-en-3-one, and 5α,14β,17α-pregnane-3β,17,20-triol 3,20-diacetate.

2. The compound according to claim 1, wherein

R$_1$ is O;

R$_2$, R$_3$, R$_5$, R$_6$, R$_7$, R$_9$, R$_{10}$, R$_{11}$, R$_{12}$, and R$_{14}$ all are hydrogen;

R$_4$ is H or methyl;

R$_8$ is methyl;

R$_{13}$ is hydrogen, or C$_{1-2}$(alkyl) with the configuration at carbon atom 20 being S;

R$_{15}$ is H or (C$_{1-15}$)acyl;

and wherein a double bond is present between carbon atoms 4 and 5, and optionally also between carbon atoms 9 and 10.

3. A pharmaceutical composition comprising an androgenically effective amount of a compound satisfying the structural formula:

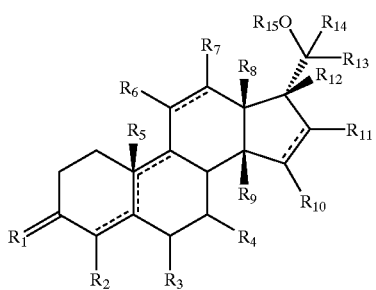

Formula I wherein
- $R_1$ is O, (H,H), (H,OR), or NOR, with R being hydrogen, $(C_{1-6})$alkyl, or $(C_{1-6})$acyl;
- $R_2$ is hydrogen, $(C_{1-6})$alkyl, or halogen;
- $R_3$ is hydrogen, $(C_{1-6})$alkyl, $(C_{2-6})$alkenyl, or $(C_{2-6})$alkynyl;
- $R_4$ is hydrogen, halogen, or cyano; or $R_4$ is $(C_{1-6})$alkyl, $(C_{2-6})$alkenyl, or $(C_{2-6})$alkynyl, each optionally substituted by hydroxy, $(C_{1-4})$alkoxy, oxo, halogen, or cyano;
- $R_5$ is hydrogen, or $(C_{1-6})$alkyl;
- $R_6$ is hydrogen, $(C_{1-6})$alkoxy, or halogen; or $R_6$ is $(C_{1-6})$alkyl, $(C_{2-6})$alkenyl, $(C_{2-6})$alkynyl, a $(C_{1-6})$alkylidene group, or a $(C_{2-6})$alkenylidene group, each optionally substituted by hydroxy, $(C_{1-4})$alkoxy, oxo, halogen, or cyano;
- $R_7$ is hydrogen, or $(C_{1-6})$alkyl;
- $R_8$ is $(C_{1-6})$alkyl;
- $R_9$ is hydrogen, halogen or cyano; or $R_9$ is $(C_{1-6})$alkyl, $(C_{2-6})$alkenyl, or $(C_{2-6})$alkynyl, each optionally substituted by hydroxy, $(C_{1-4})$alkoxy, oxo, halogen, or cyano;
- $R_{10}$ is hydrogen, $(C_{1-6})$alkoxy, halogen, or cyano; or $R_{10}$ is $(C_{1-6})$alkyl, $(C_{2-6})$alkenyl or $(C_{2-6})$alkynyl, each optionally substituted by hydroxy, $(C_{1-4})$alkoxy, oxo, halogen, or cyano; or
- $R_{10}$ together with $R_{11}$ and the carbon atoms at which they are placed form a cyclopropane ring;
- $R_{11}$ is hydrogen, $(C_{1-6})$alkoxy, halogen, or cyano; or $R_{11}$ is $(C_{1-6})$alkyl, $(C_{2-6})$alkenyl or $(C_{2-6})$alkynyl, each optionally substituted by hydroxy, $(C_{1-4})$alkoxy, oxo, halogen, or cyano; or
- $R_{11}$ together with $R_{10}$ and the carbon atoms at which they are placed form a cyclopropane ring;
- $R_{12}$ is hydrogen, hydroxy, halogen, or cyano; or $R_{12}$ is $(C_{1-6})$alkyl, $(C_{2-6})$alkenyl, or $(C_{2-6})$alkynyl, each optionally substituted by hydroxy, $(C_{1-4})$alkoxy, oxo, halogen, or cyano;
- $R_{13}$ and $R_{14}$ are independently hydrogen, cyano, or phenyl, the latter optionally substituted by hydroxy, $(C_{1-4})$alkoxy, $(C_{1-4})$alkyl or halogen; or $R_{13}$ and $R_{14}$ are independently $(C_{1-6})$alkyl, $C_{2-6})$alkenyl, $(C_{3-6})$cycloalkyl, $(C_{5-6})$cycloalkenyl or $(C_{2-6})$alkynyl, each optionally substituted by hydroxy, $(C_{1-4})$alkoxy, phenyl, oxo, halogen, or cyano; or $R_{13}$ and $R_{14}$ together with the carbon atom at which they are placed form a $(C_{3-6})$cycloalkane ring or a $(C_{5-6})$cycloalkene ring;
- $R_{15}$ is hydrogen, $SO_3H$, $(C_{1-6})$alkyl, or $(C_{1-15})$acyl; and the dotted lines indicate optional bonds, and a pharmaceutically acceptable carrier or diluent.

4. A method of treating androgen insufficiency in a patient comprising administering to the patient an effective amount of the compound of claim 1 to overcome the androgen insufficiency.

5. A method of male contraception comprising administering to the male an effective amount of the compound of claim 1.

* * * * *